United States Patent
Shen et al.

(10) Patent No.: US 9,909,953 B2
(45) Date of Patent: Mar. 6, 2018

(54) METHOD AND APPARATUS FOR NON-DESTRUCTIVE DETECTION OF TIRE ANOMALIES

(71) Applicants: Compagnie Generale des Etablissements Michelin, Clermont-Ferrand (FR); Michelin Recherche et Technique S.A., Granges-Paccot (CH)

(72) Inventors: Qin Shen, Gastonia, NC (US); Gheorghe Bunget, Charlottesville, VA (US); Frank Gramling, Simpsonville, SC (US); David Judd, Mauldin, SC (US); Thomas Kurfess, Clemson, SC (US)

(73) Assignee: Compagnie Generale des Etablissements Michelin, Clermont-Ferrand (FR)

( * ) Notice: Subject to any disclaimer, the term of this patent is extended or adjusted under 35 U.S.C. 154(b) by 75 days.

(21) Appl. No.: 15/033,854

(22) PCT Filed: Nov. 5, 2013

(86) PCT No.: PCT/US2013/068513
§ 371 (c)(1),
(2) Date: May 2, 2016

(87) PCT Pub. No.: WO2015/069218
PCT Pub. Date: May 14, 2015

(65) Prior Publication Data
US 2016/0282227 A1     Sep. 29, 2016

(51) Int. Cl.
G01M 17/02     (2006.01)
G01N 29/04     (2006.01)

(52) U.S. Cl.
CPC ........ G01M 17/025 (2013.01); G01N 29/045 (2013.01)

(58) Field of Classification Search
None
See application file for complete search history.

(56) References Cited

U.S. PATENT DOCUMENTS 3,967,498 A     7/1976   Pezzillo
4,297,876 A *   11/1981  Weiss ................ G01M 17/025
                                                          73/146

(Continued)

OTHER PUBLICATIONS

European Patent Office, Supplementary European Search Report, Communication from European Patent Application No. 13897019.9, dated May 30, 2017, 8 pages, European Patent Office, published in Munich, Germany.

(Continued)

*Primary Examiner* — Peter Macchiarolo
*Assistant Examiner* — Jermaine Jenkins
(74) *Attorney, Agent, or Firm* — Neal P Pierotti

(57) ABSTRACT

An impact-acoustic method for testing a tire is provided along with a tire anomaly detection system in which an actuatable impactor is provided with an acoustic transducer and a force transducer. A plurality of discriminator quantities is calculated from acoustic signals and force signals and the calculated discriminator quantities are compared with stored discriminator quantities to determine whether an anomaly is present in the tire.

26 Claims, 23 Drawing Sheets

(56) References Cited

U.S. PATENT DOCUMENTS

| | | | |
|---|---|---|---|
| 4,479,386 A | 10/1984 | Beggs | |
| 4,799,375 A | 1/1989 | Lally | |
| 5,894,086 A * | 4/1999 | Jao | G01M 17/025 |
| | | | 73/146 |
| 6,381,547 B1 * | 4/2002 | Heirtzler | G01M 17/025 |
| | | | 702/35 |
| 6,832,513 B2 * | 12/2004 | Weiss | G01M 17/02 |
| | | | 73/146 |
| 6,837,102 B2 * | 1/2005 | Weiss | G01M 17/02 |
| | | | 324/558 |
| 6,907,777 B2 * | 6/2005 | Weiss | G01M 17/02 |
| | | | 73/146 |
| 2004/0016293 A1 | 1/2004 | Weiss | |

OTHER PUBLICATIONS

International Search Report with Written Opinion dated Mar. 27, 2014.

Translation of State Intellectual Property Office of P.R. China, Notification of First Office Action for Chinese patent application No. 201380080288.X, dated Sep. 26, 2017, six pages, published in China.

\* cited by examiner

METHOD AND APPARATUS FOR NON-DESTRUCTIVE DETECTION OF TIRE ANOMALIES

TECHNICAL FIELD

The presently disclosed invention is generally directed to non-destructive testing methods and devices for tire casings. More particularly, the presently disclosed invention is directed to applying impact-acoustic methods to accurately detect tire anomalies and irregularities prior to a retreading process.

BACKGROUND

When tires become worn, they may be restored with new tread bands or tread layers during a retread process. Retreading is a restoration or re-manufacturing process that not only extends the service life of the tires, but also is significantly less expensive than manufacturing new tires. Since recycling and retreading are key for reducing costs and energy inherent in the manufacturing of tire casings, an effective retread necessitates a tire casing with good structural integrity (i.e., without internal anomalies or irregularities).

Prior and/or subsequent to retreading of a truck tire casing, a non-destructive testing (NDT) method may be used to detect and locate internal anomalies. Such anomalies may include, but are not limited to, cracks, voids, delaminated layers and/or foreign material. Numerous attempts have been made using advanced NDT techniques, and several types of inspection procedures have been employed and commercialized by the tire remanufacturing industry. For example, industrial radiography with X-ray is a real-time method for tire inspection. This inspection method provides high sensitivity to anomalies such as foreign materials and porosity (e.g., due to variations in radiation intensity of the X-rays penetrating through different materials). Smaller bonding irregularities, however, may be difficult to detect since the penetration capability of the X-rays is dependent on material density. Further inspection procedures are therefore required to investigate those conditions which are not detectable by X-rays.

Another known inspection method utilizes ultrasound vibration at higher frequencies (usually 1-10 MHz used in the tire industry) that attenuates much faster in the air than audible sound. The ultrasonic method can be used to examine abnormal cord spacing, belt anomalies or changes in the wall thickness of a tire. Automation of this testing procedure is complicated by the need for a coupling medium between the transducer and the object surface. In addition, the ultrasonic method requires extensive training and experience to interpret the data, therefore inhibiting the application of this inspection method in high-yield inspection environments.

Shearography, which is widely used for tire casing inspection, can detect various types of anomalies such as voids and de-laminations in belts and sidewalls. Using shearography, a tire is first scanned by a laser light placed in the center of the tire casing under normal atmospheric pressure to obtain a baseline photograph. The tire casing is placed in a vacuum. If there is an irregularity such as an air filled void, the low pressure around the casing causes the air trapped in the void to expand. A "stressed" photograph is obtained by scanning the tire casing under vacuum, which photograph is compared with the baseline photograph to produce a fringe pattern. An internal variance usually induces strain concentrations under stress that can cause differences between the two images and be translated into an anomaly in the fringe pattern. Shearography therefore correlates internal anomalies with the variances in displacement gradients. Interpretation of shearograms often requires a skilled operator, and shearography devices may require large fiscal and temporal expenditures, particularly when large batches of tires require examination.

Therefore, a reliable and cost-effective NDT technique is demanded that accurately determines the internal anomalies in a tire casing and does so predictably in a variety of production environments.

SUMMARY

An impact-acoustic method for testing a tire is provided that includes providing an actuatable impactor disposed proximate an impact area whereupon the impactor strikes the tire. An acoustic transducer is disposed proximate the impact area on a common side of the tire with the impactor, with the acoustic transducer receiving one or more sound waves generated when the impactor strikes the impact area and generating corresponding acoustic signals. A force transducer is disposed proximate the impact area for measuring one or more dynamic forces and generating corresponding force signals indicative of impact force. A tire is provided on a test platform such that the impactor strikes the impact area during actuation thereof. A plurality of discriminator quantities is calculated from the acoustic signals and the force signals. The calculated discriminator quantities are compared with stored discriminator quantities to determine whether an anomaly is present in the tire.

In some embodiments, one or more computing devices may be provided in communication with at least one of the acoustic and force transducers. The computing devices may include instructions for performing at least one of transferring data from at least one of the transducers and controlling one or both transducers either directly or indirectly. In additional embodiments, each of the calculated discriminator quantities and the stored discriminator quantities includes one or more quantities of peak impact force, impact duration, area under initial contact sound, free vibration energy, accumulative power ratio, power spectrum local peak magnitude and accumulated spectral energy. The stored discriminator quantities may be representative of tire integrity of previously tested tires.

In some embodiments, at least one of the acoustic transducer and the force transducer is a network-connected device and the method further includes providing a platform. The platform may include a server in communication with at least one network-connected device and an engine. The engine may be configured to perform at least one of accessing at least one artificial neural network (ANN) for training and predicting anomaly indicators; recording test data as each tire is tested; computing discriminator quantities based upon the detected sound waves and the force signals; comparing at least one stored discriminator quantity with at least one calculated discriminator quantity; and based upon the comparing, determining tire integrity.

A tire anomaly detection system is also provided that includes a tire support system having a test platform and an impact system. The impact system includes an actuatable impactor disposed proximate an impact area whereupon the impactor strikes a tire placed on the test platform. The impact system also includes an acoustic transducer disposed proximate the impact area on a common side of the tire with the impactor. The acoustic transducer receives one or more sound waves generated when the impactor strikes the impact area and generates corresponding acoustic signals indicative of the received sound waves. A force transducer disposed proximate the impact area measures one or more dynamic forces and generates corresponding force signals indicative of impact force. A plurality of discriminator quantities are calculated from the acoustic signals and the force signals. The calculated discriminator quantities are compared with stored discriminator quantities to determine whether an anomaly is present in the tire.

A tire anomaly detection system is also provided that includes a tire support structure for supporting a tire during testing. An impactor is disposed proximate the tire for impacting the tire at one or more locations. An acoustic transducer is disposed proximate the impactor for receiving a sound wave when the impactor contacts the tire. A force transducer measures one or more dynamic forces at locations of impactor contact and generates corresponding force signals indicative of impact force. The system also includes one or more computing devices each having a processor with instructions for calculating a plurality of discriminator quantities from the sound wave and the force signals and instructions for comparing the calculated discriminator values with stored discriminator values indicative of an anomaly in the tire.

Other aspects of the presently disclosed apparatus will become readily apparent from the following detailed description.

BRIEF DESCRIPTION OF THE DRAWINGS

The nature and various advantages of the present invention will become more apparent upon consideration of the following detailed description, taken in conjunction with the accompanying drawings, in which like reference characters refer to like parts throughout, and in which.

DETAILED DESCRIPTION

The presently disclosed invention is directed to employment of impact-acoustic and impact-echo methods for tire anomaly detection. Such methods, as illustrated in FIG. 1, are based upon applying a local disturbance on a structural surface while recording the resulting airborne sound waves.

Figure 1A:
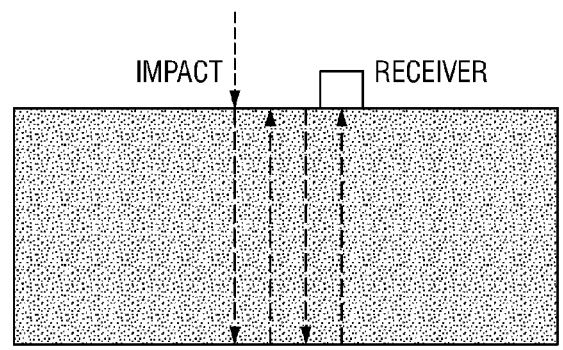
FIG. 1 shows schematic representations of impact-acoustic methods as generally known.

In an impact-echo method, a disturbance is applied at a point on the surface of a solid while recording the resulting stress waves that have approached a transducer (see FIG. 1(a)). The basic methodology of the impact-echo method is that the propagation of stress waves can be different due to the existence of internal anomalies in the structure. Impact-echo is essentially a contact NDT method, thus requiring careful consideration of how the transducer approaches and retracts from the testing surface automatically. Continuous testing around a tire circumference is realized thereby.

Figure 1B:
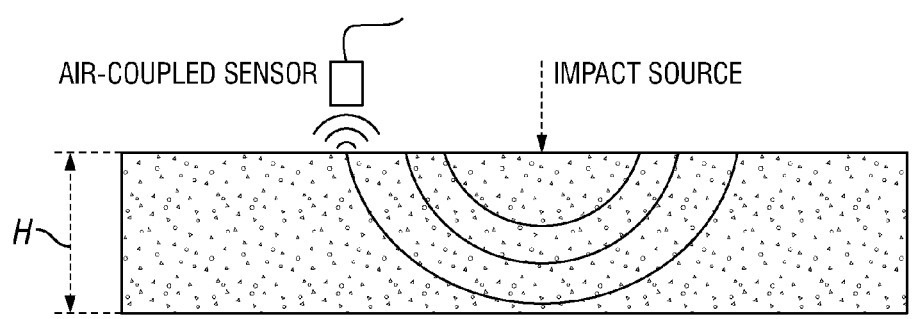

Impact-acoustic methods replace the contact transducer with an air-coupled transducer, which records the sound waves generated by the vibration of the neighboring structure excited by an impact (see FIG. 1(b)). The transducers (e.g., one or more microphones) record the sound waves generated by vibration of the neighboring structure excited by a short impact. In some embodiments, noise-cancelling microphones or phase-arrayed microphone noise cancelling algorithms can be implemented to enhance the quality of the received microphone signals. The propagation of impact-induced transient stress waves in the test object varies due to the presence of internal anomalies such as disbanding or de-laminations. Piezoelectric based transducers measure the surface displacement response by contact with the test object. In the case of impact-acoustic methods, the material undergoes very small strains and thus only the initial tangent modulus is relevant.

The presently disclosed invention facilitates investigation and analysis of the dynamic response of rubber composite structure to an impact. The impact force signal has been identified as a useful means to characterize the impact response from testing on a rubber composite structure. Furthermore, the impact induced acoustic signal can be studied in two separate stages: (1) initial contact sound due to local deformation at the impact region; and (2) ringing sound due to free vibration of the structure. Both parts of the impact sound have been demonstrated as related to the tire's structural properties, which can be used to determine the existence of the structural anomalies. An integrated approach by measuring both impact force and the impact sound has been adopted herein, and analytical modeling explains the relationship between the impact acoustic signals and the internal cracks.

The sound pressures monitored by a transducer near the impact location correspond to the movement history of the target. The initial stage of the acoustic signal is due to the deformation and restitution of the target within the duration of impact. The rest of the acoustic signal is produced by the free vibration of the structure. The embedded internal anomalies dissipate the energy from the resonant modes to other flexural modes, which can be observed in the frequency domain using frequency analysis such as the Fast Fourier Transform (FFT). It is understood that other analyses may be employed without departing from the scope of the present disclosure.

The presently disclosed invention employs an impact-acoustic method for nondestructive testing (NDT) for internal cracks in a rubber composite structure, such as that found in a tire. This approach is an effective and economical alternative to the current NDT methods for tire casing integrity inspection. In some embodiments, the impact force signal and the resultant acoustic signal are separate aspects of the impact acoustic signals under consideration. As presently disclosed herein, a contact dynamics model is developed based on Hertz's impact theory and modified for rubber composite materials. This model generates prediction of major impact dynamics quantities, which are theoretically proven to be sensitive to the existence of internal structural cracks. For the purpose of applying the impact acoustic method for inspection of tire casing integrity, models are developed for simplified tire structures. The models assume a cubic shape fabricated from rubber compound material without reinforcements. The prepared cubic rubber samples are designed to roughly approximate the profile of a sectional tire casing and the cracks embedded at the belt edge in a shoulder area.

Energy-based analysis of the structure is another useful approach to understand the effect of embedded anomalies on the impact behavior. The differences of the material properties of the two colliding bodies result in energy loss, which is dependent upon various properties including, but not limited to, stiffness, density and shape. Based upon the modeling of energy loss in the impact process, it was analytically and experimentally shown that the intensity of sound excited by flexural vibration after impact can be used as an indicator of structural integrity.

Significant research based on impact-acoustic methods is driven by the fact that the human ear can capture the difference in the sound while tapping or hammering the tested structure. An automation of this procedure would make inspection more efficient, less subjective and operator independent. It has also been reported that the feedback from vibrating hammers or other tools, after the impact, is also relevant to the structural difference. Thus, in some embodiments, one or more microphones sense the sound waves. An impactor made with a load cell tip records the vibration feedback as well.

Based upon comprehensive theoretical analysis of the impact acoustic signals, discriminators can be extracted from the impact force signal and the acoustic time- and frequency-domain signal. These discriminators may be verified as indicators of internal anomalies in both simplified cubic rubber structures and complicated tire casings. Integration of the extracted discriminators helps to mitigate the deficiencies and noise caused by relying heavily on a single discriminator, while providing an integrated index that accurately identifies the anomaly conditions. Development of a data fusion method by weighted averaging of the discriminators allows generation of a single anomaly index as an indicator of the integrity of inspected tires.

The presently disclosed invention implements measurements of time domain and frequency characteristics as inputs to an artificial neural network (ANN). As used herein, an "artificial neural network" (or "ANN") refers generally to one or more models that are capable of pattern recognition, forecasting and/or data compression. The ANN is trained using measurements of sample tires with known characteristics.

The presently disclosed invention contemplates design and fabrication of an automated test platform; experimental investigation and algorithm determination; and ANN analysis including offline database training and online sample evaluation. An integrated approach by measuring both impact force and impact sound is adopted by the presently disclosed invention, and analytical modeling is employed to represent the relationship between the impact acoustic signals and the internal anomalies. Experimental validations are performed on both the rubber structure solved by the analytical model and the complex tire casings.

As disclosed herein, a novel set of discriminators is used in combination with a force transducer. An overall characterization of the tire as being suitable for retreading is sought, rather than seeking to localize individual variances. The specific orientation of transducers (e.g., microphone and load cell) and the selection of discriminator functions are a result of extensive experimentation aided by finite element modeling. Where conventional impact-acoustic and impact-echo methods use microphones or accelerometers to detect internal tire anomalies, the presently disclosed invention implements a combination of impactor, accelerometer, microphone and analysis algorithms to detect a range of anomaly sizes, types and locations.

Figure 2:
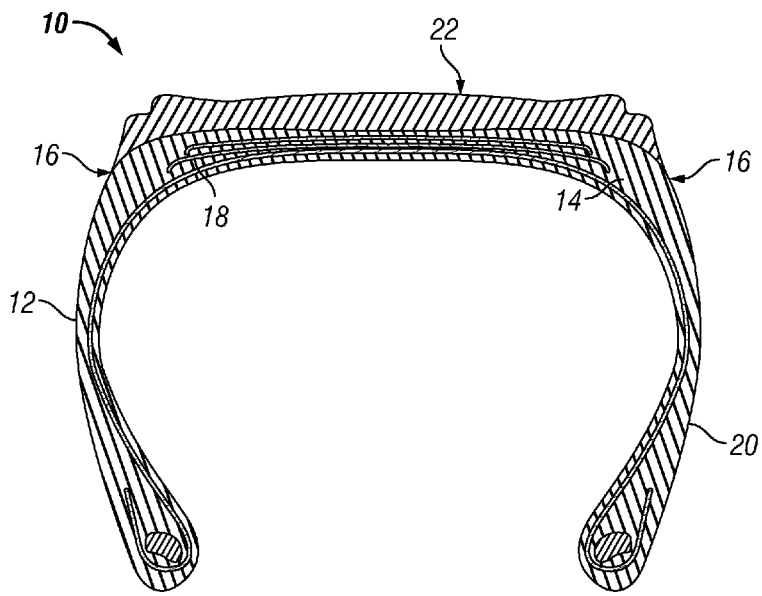
FIG. 2 shows an exemplary tire assembly having an exemplary casing for testing as presently disclosed.

Referring to the figures, wherein like numbers represent like elements, FIG. 2 shows an exemplary tire 10 having a tire casing 12 with a crown section 14, shoulders 16, reinforcement 18 and sidewall 20. Crown section 14 may have been buffed or otherwise worked to provide a prepared bonding surface to which a laterally extending tread 22 can be bonded (e.g., via one or more bonding layers). Buffing old tread off of the tire in preparation for retreading removes rubber that is typically replaced during the retreading process as part of the undertread portion of the tread that is bonded to the carcass. The material that is removed from the tire to be retreaded creates waste that is discarded and then replaced with new material that is bonded to the tire carcass during the retreading process. One or more tread elements (not shown) may be integral with tread 22 in a variety of configurations as known in the art. It is therefore understood that the configuration of tread 22 is not limited to that shown herein and that a variety of tread configurations are amenable for use with the carcass.

Theoretical Basis for Impact Acoustics

Impact-generated dynamic response results in compression and rarefaction of the surrounding air, thus forming concentric wave fronts of increased and decreased pressure that originate from the point of contact. The sound pressure levels monitored by a microphone near the impact location correspond to the movement history of the target. The initial stage of the acoustic signal is due to the deformation and restitution of the target within the duration of impact. The rest of the signal is due to the free vibration of the target.

The area under an initial negative peak in the sound waveform is an indicator of the energy transmitted from the kinetic energy of the impactor to the deformation of the target, which is an alternative way to measure the energy dissipation during the impact process. The power ratio method used in the previous phase provides a solution to extract useful attributes from the frequency-domain of the sound waveforms. It has been stated that the free vibrations of the structure contain multiple modes, and the existence of the internal anomalies will dissipate the resonant energy to other flexural modes. By identifying the resonant frequencies of the structure and observing the change of the power spectral density (PSD) in the other frequencies, it is possible to reveal the effect of anomalies and variances.

Basis for Impact Dynamics

Figure 3:
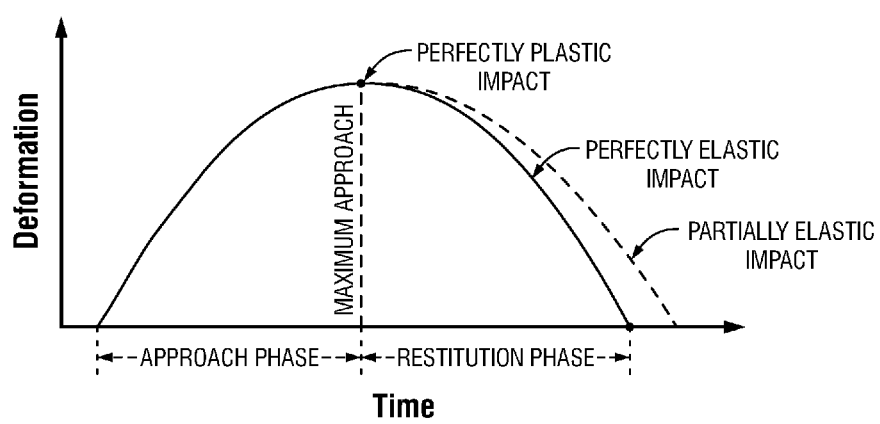
FIG. 3 shows an exemplary deformation history of different impact regimes as generally known.

Referring to FIG. 3, impact behavior usually involves the description of the impact momentum change, transient stresses, contact forces and deformations. Based upon impact-induced transient stresses, the behavior of impacted solids can be divided into different regimes. For stresses below the yield strength, materials behave elastically. Two extremes of this regime are a perfectly elastic impact and a perfectly inelastic impact.

The deformation history of an impact normally consists of an approach phase and a restitution phase (see FIG. 3). The restitution coefficient e introduced by Newton is a dimensionless quantity, usually between 0 and 1. It is a measure of the energy loss during impact, defined as the ratio of the relative separation velocity after impact to the relative approach velocity before impact. For a perfectly elastic impact, the kinetic energy of the system is fully conserved, thus e=1. For a perfectly inelastic impact, the two bodies coalesce and move as a single mass after impact, thus e=0. Most impacts, however, are intermediate between perfectly elastic and perfectly inelastic corresponding to 0<e<1 (referred to "partially elastic" impact).

In the presently disclosed invention, an impact-acoustic method is observed in the regime of partially elastic impact. In this situation, part of the impact energy is transmitted into the impacted target and the rest conserved into the impactor. Three major interests are normally discussed in this regime: contact mechanics, impact energy loss and elastic wave propagation. Contact mechanics is mainly concerned with contact force, deformation and impact duration. Impact energy loss can be addressed by the impulse momentum theory based on classical mechanics, given the knowledge of the coefficient of restitution. Elastic wave propagation in the impacted solid transforms into vibrations and relies on the wave propagation approach. Effective models of these parameters permit application of their effects for anomaly detection. A contact mechanics model describing the impact dynamics associated with the impact-acoustic signal is generated. The model quantities are then correlated with the presence of internal irregularities in the impacted target to determine the anomaly discriminators.

To derive an analytical solution for the partially inelastic impact dynamic process, the restitution coefficient e is a significant parameter. In the case of rubber materials that involve a non-negligible, nonlinear hysteretic damping effect, impact energy loss is associated with the hysteretic damper. There are various experimental approaches to determine the restitution coefficient e as known in the art. It is understood that the combined coefficient of restitution e is related to like-material coefficients $e_1$, $e_2$ and respective elastic moduli, by the equation:

$$e = \frac{e_1 E_2 + e_2 E_1}{E_1 + E_2}$$

Judging from the expression, the structural stiffness can influence the coefficient of restitution. If $e_1 > e_2$ (e.g., a steel impactor and a rubber target), then a reduced target stiffness ($E_2$) can result in a smaller e, which means more energy is lost. Theoretically, the existence of an internal anomaly (e.g., an internal crack or commensurate abnormality) can reduce the structural stiffness, and the flexural vibration introduced by the crack will dissipate the total energy. The energy loss factor λ can be calculated on the basis of the coefficient of restitution as:

$$\lambda = 1 - e^2$$

This measure of energy dissipation is similar to the rebound resilience R, which is an important index that estimates the loss properties of rubber. The resilience R is usually measured from a drop test, which can be determined by taking down the drop height $h_1$ and rebound height $h_2$, then derived as:

$$R = e^2 = h_2/h_1$$

In this case, λ can be written as:

$$\lambda = 1 - R$$

First, a general case of a spherical solid impacting an isotropic integral target is considered, and a single degree-of-freedom spring-mass-damper system is relied upon to describe the impact dynamics model. The mass and displacement of the impactor are respectively denoted as $m_1$ and $x_1$ and those of the target are respectively denoted as $m_2$ and $x_2$. The relative deformation due to local compression at the center of the contact surface is:

$$\alpha = x_1 - x_2$$

Based on the energy method by equating the energy loss derived from the momentum impulse approach and the one derived from hysteretic damping at time t, the penetration velocity can be found.

Considering the energy distribution during the impact process, the differences of the material properties of the two contact bodies result in a certain amount of energy loss. Such energy loss is dependent on various properties including, but not limited to, stiffness, density and shape. The energy loss factor can be used as an indicator of the internal anomalies in the target since an embedded delamination can greatly reduce the structural stiffness. An intuitive method to measure this energy loss is to record the initial and final velocities of the impactor. Therefore, the energy loss λ can be expressed as:

$$\lambda = 1 - V_f^2/V_i^2$$

This measure of energy dissipation is similar as the rebound resilience R which is an important index that estimates the loss properties of rubber.

Artificial Neural Network Technique

Artificial Neural Networks (ANNs), also referred to herein as neural networks (NNs) are relatively simple and effective tools that capture and represent complex and non-linear input/output relationships. NNs include interconnected layers of neurons with each neuron containing three sections: the node for receiving an input, connectivity for passing along values and weights that are multipliers for those values. ANNs having sufficient numbers of layers and nodes are able to accommodate the nonlinearities of processes, boundary conditions and other parameters that may control measured potentials and impedances.

Figure 4:
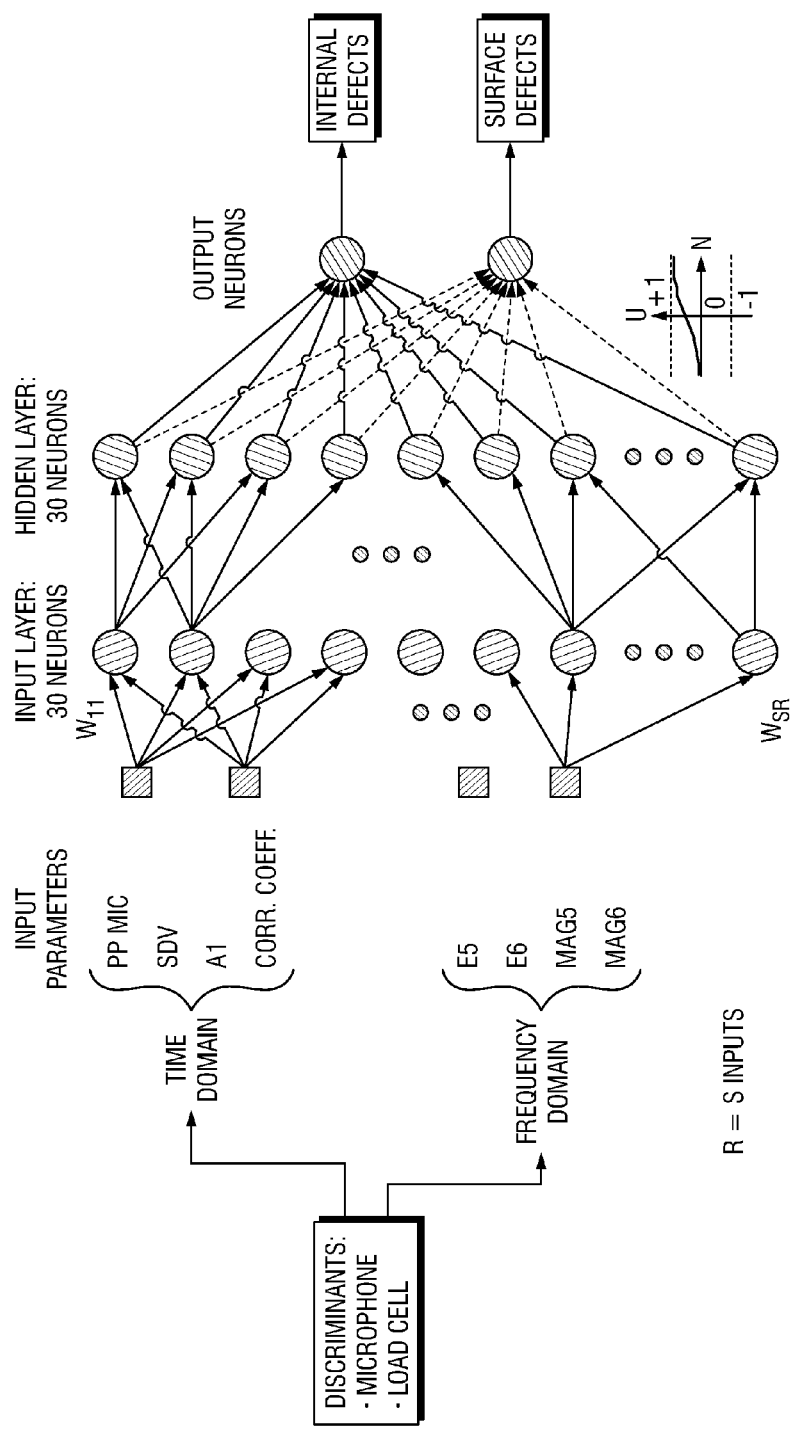
FIG. 4 shows exemplary stochastic modeling using an exemplary neural network as presently disclosed.

In the presently disclosed invention, using impact-acoustic test data, an exemplary NN algorithm was developed to interpret the measured indicators both from time and frequency domains to predict the extent and location of internal anomalies and variances. A variety of NN types may be employed for preliminary tire anomaly evaluation, including but not limited to a feed forward neural network with a back propagation algorithm. As shown in FIG. 4, basic rules may be used to establish the preliminary network design and neurons in the hidden layer based upon 8 inputs and 2 outputs, yielding approximately 30 neurons in the each of the hidden layers. It is understood that other NN types may be employed using a different number and variety of inputs to derive a different number and variety of outputs.

As shown further in FIG. 4, this exemplary NN computational algorithm requires a training process in order to determine the connection weights which later are used to estimate the tire anomaly with a sensor system. Specifically, a set of known values (targets) of irregular areas and locations are compared with the output of the NN. The weights are adjusted iteratively until the error is minimized. Once the model is trained, the resultant weights are set (or "frozen") and implemented as a prediction method for tire condition. In the example shown, the estimated number of training data sets needed was upwards of 800 (although this may vary when training other NN types). The outputs of the NN were placed into two bins: surface defects (e.g., cracks) and internal defects.

Sensitivity Analysis

Sample Preparation and Material Properties

Figure 5:
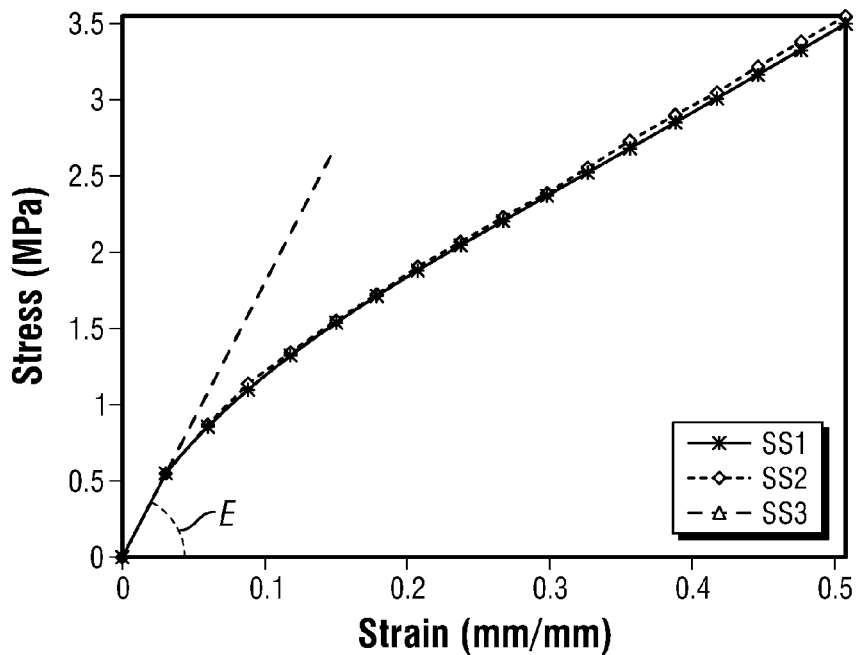
FIG. 5 shows exemplary stress-strain curves measured on a sample rubber composite material.

The material properties of the rubber target (i.e., the tire) and the impactor have been determined experimentally. It was assumed that the strain in the impact-acoustic is so low and varies in such a small range that the rubber material can be treated as a linear material with a low strain area of the stress-strain curve in FIG. 5. The rubber measured in the stress testing is equivalent to (or the same as) the material used around the belt edges in the tire shoulders. Material properties of the rubber target and an aluminum impactor are given in Table 1:

TABLE 1

Material Properties of Sample Rubber and Aluminum Impactor

|  | Sample Rubber | Aluminum |
| --- | --- | --- |
| Density (kg/m$_3$) | 1143 | 2700 |
| Elastic Modulus (E) MPa | 17.9 | 0.7e5 |
| Poisson's Ratio (ν) | 0.49 | 0.3 |

The loss tangent tan δ is strongly dependent on the frequency of excitation and the temperature. A rough approximation of tan δ is to relate with the rebound resilience R as:

$$\tan(\delta) = -\ln(R)/\pi$$

The rebound resilience R of the sample rubber material is measured through the rebound test as 0.25, therefore the loss tangent can be calculated as:

$$\tan(\delta) = -\ln(0.25)/\pi \approx 0.44$$

Sensitivity Analysis of the Integral Model

The contact dynamics model for an integral solid structure is further analyzed in order to learn the effect of each influencing factor on the predicted discriminators. The factors considered for sensitivity analysis are: the impact speed ($V_i$), the impactor's mass ($m_1$), the target mass ($m_2$), the impactor's stiffness ($E_1$) and the target stiffness ($E_2$). A set of trial parameters in Table 2 is used initially to obtain a baseline scenario. Three discriminators are monitored: maximum impact force ($F_{max}$), impact duration (τ) and maximum contact deformation ($\alpha_{max}$):

TABLE 2

Baseline Influencing Factors

|  | $V_i$ (m/s) | $m_1$ (kg) | $m_2$ (kg) | $E_1$ (Pa) | $E_2$ (Pa) |
| --- | --- | --- | --- | --- | --- |
| Baseline | 1.85 | 0.0045 | 1.6483 | 70e9 | 17.9e6 |

Each variable is multiplied by a factor N that ranges from 0.1 to 2. The baseline values correspond to N=1. $F_{max}$, τ and $\alpha_{max}$ are calculated for each influencing factor that is individually varied, respective plots of which are presented in FIGS. 6, 7 and 8. It can be observed from the plots that $m_2$ and $E_1$ have greater orders of magnitude than $m_1$ and $E_2$.

Figure 9:
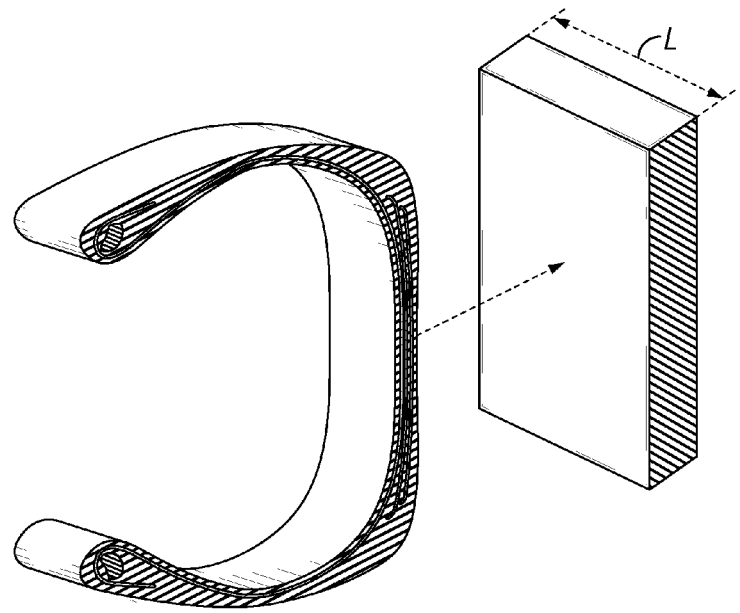
FIG. 9 shows an exemplary model approximation of an exemplary tire section.

The sensitivity analysis of impact dynamics on the discriminators provides a theoretical basis for a model used to approximate the shape of a tire casing. An exemplary cubic rubber block used for approximating a section of tire casing is shown in FIG. 9. The assumption made for the model (i.e., that the target mass can be treated as infinite and stationary) has been observed as valid. One prerequisite to simplify the model is to assume that the applied impact only affects the mechanical dynamics within a limited local area of materials around the contact region. The two sidewalls were eliminated in the simplified model. Since the mass of the rubber block is much greater than that of the impactor, the error introduced by the approximation can be neglected. The curvature of the tread was deemed to be zero for a small curved segment considering that the boundary contours have minor effect on impact response. The vertical height of the cube simulates the shoulder to shoulder distance, and the horizontal thickness corresponds to the distance from tread surface to inner carcass.

The impact velocity, the mass of the impactor and the stiffness of the target structure are all influential factors on the discriminators. All of the monitored dynamic quantities are very sensitive to the variation in $V_i$. This relationship suggests maintenance of a constant $V_i$ throughout impact tests for the purpose of anomaly identification, so that the fluctuations introduced by variations in $V_i$ can be mitigated as much as possible.

Moreover, the mass of the impactor $m_1$ influences the discriminators much more dominantly than the target mass. This observed conclusion enables acquisitions of the sensitivities of the curvatures of the colliding bodies (i.e., the contact radii $r_1$ and $r_2$). According to the relationship between the colliding bodies' masses $m_1$, $m_2$ and the equivalent contact radii $r_2$, it is observed that the curvature of the target surface affects the discriminators much less than that of the impactor surface. The surface curvature of the tire shoulder can thus be deemed as zero, which is equivalent to a flat surface perpendicular to the applied impact. Alternatively, the sensitivity plots show that the impactor's radius $r_1$, relating to the impactor's mass $m_1$, influences all three discriminators. The effects of the impact velocity $V_i$ and the impactor's radius $r_1$ on the impact duration will in turn be reflected on the frequency features of the impact responses.

Figure 6:
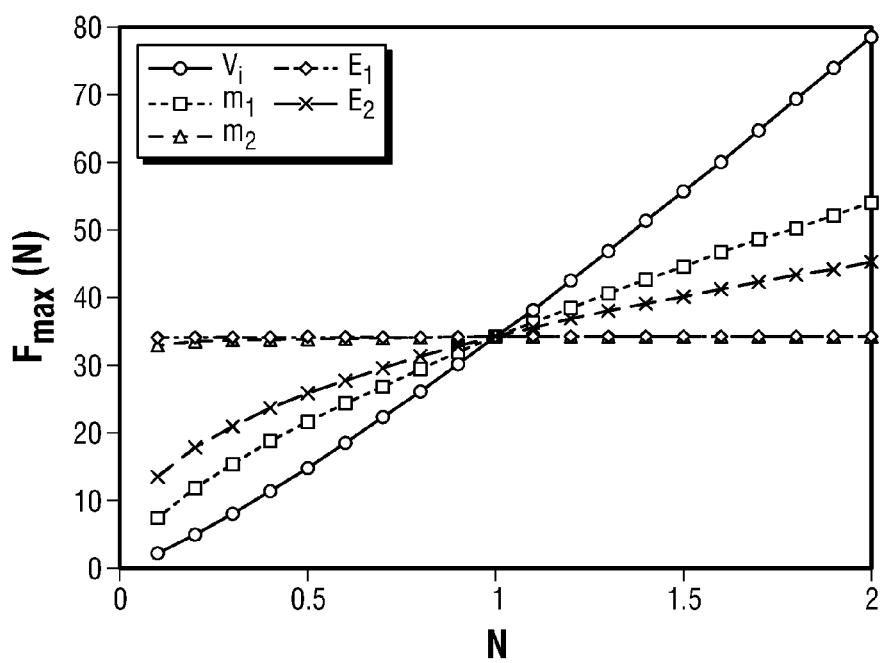
FIG. 6 shows an exemplary plot of integral model sensitivity of influencing factors on maximum impact force.
Figure 7:
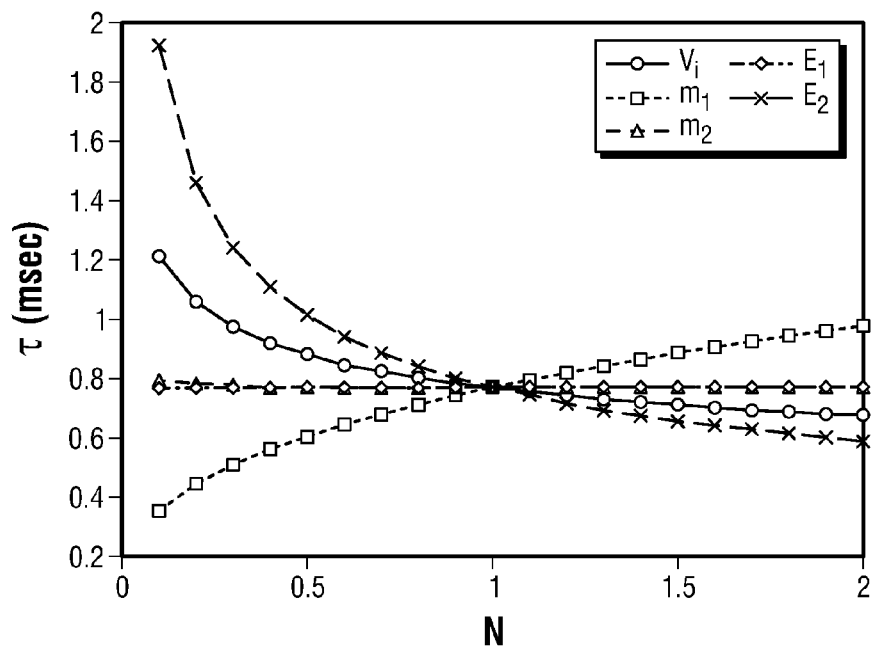
FIG. 7 shows an exemplary plot of integral model sensitivity of influencing factors on impact duration.
Figure 8:
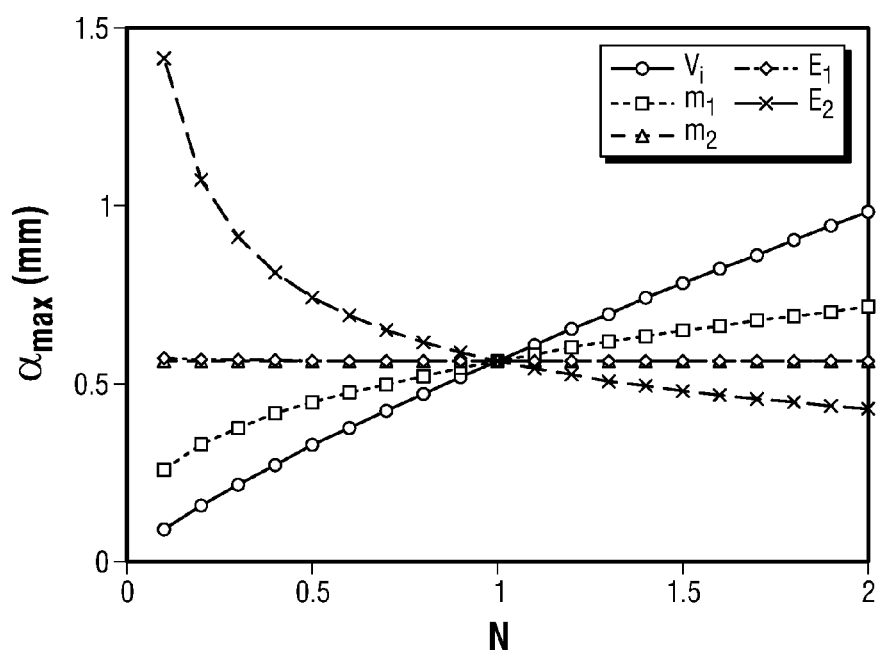
FIG. 8 shows an exemplary plot of integral model sensitivity of influencing factors on maximum contact deformation.

Another influence on the impact acoustic discriminators is the elastic modulus of the target $E_2$, which can be observed from FIGS. 6 to 8. In the case of a tire casing structure, $E_2$ is influenced by various factors including, but not limited to, embedded steel belts, quality of uniformity and foreign inclusions. Considering the prerequisite for the impact-acoustic method, which assumes that the impact induced stresses only take effect in a limited region around the contact area, the far-field reinforcements (such as steel belts) provide little change to the impact responses.

Figure 10:
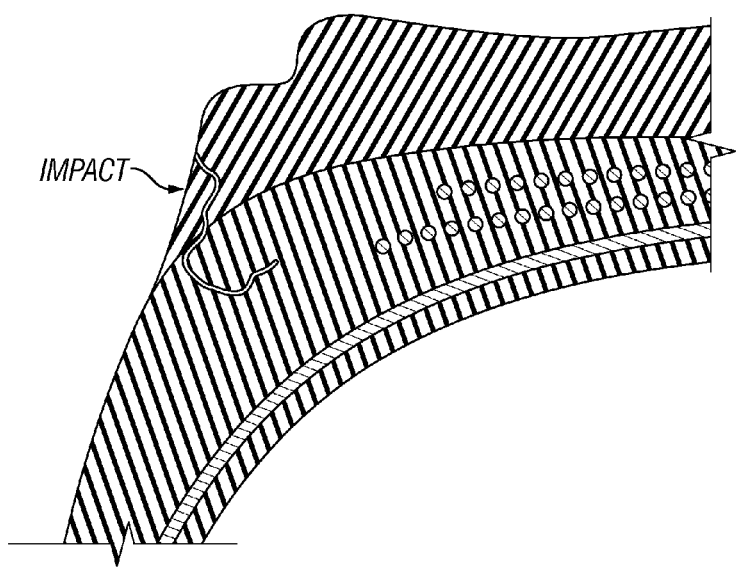
FIG. 10 shows a cross-section of an irregularity around belt edges during testing according to a presently disclosed method.

A significant factor that changes the target stiffness is attributed to variances located around the belt edges as shown in FIG. 10. As a result, the variations observed in the dynamic quantities can be attributed to the existence of embedded abnormalities. Other influential factors remain stable throughout the tests, thereby providing an indication of structural integrity.

Sensitivity Analysis of the Anomaly Model

The corresponding anomaly model has incorporated two additional parameters h and l that help to define the geometry and location of an internal abnormality. The effects of varying these parameters on impact dynamic responses need to be understood at least partly in terms of the flexural energy loss. Baseline values of the evaluated factors are given in Table 3. The four impact dynamic discriminators can be calculated for each individually varied influencing factor, respective plots of which are presented in FIGS. 11 to 14.

TABLE 3

Baseline Influencing Factors and Dimensions of Abnormality

| | $V_i$ (m/s) | $m_1$ (kg) | $m_2$ (kg) | $E_1$ (Pa) | $E_2$ (Pa) | h | l |
|---|---|---|---|---|---|---|---|
| Baseline | 1.85 | 0.0045 | 1.6483 | 70e9 | 17.9e6 | 25.4 | 25.4 |

Sensitivity analysis of the first five factors considered for the anomaly model yields similar conclusions as the integral model. The two least influential factors, $m_2$ and $E_1$, can be eliminated in the sensitivity plots. As shown herein, a clear comparison is provided between the abnormality parameters and the other five factors. It was assumed previously that variations in the target stiffness $E_2$ are attributed to the existence of at least one abnormality, which can therefore be related to the two parameters h and l. It can be seen that an increase in abnormality depth h and a decrease in abnormality length l are both equivalent to an increase in $E_2$, the elastic modulus of the target structure.

Figure 11:
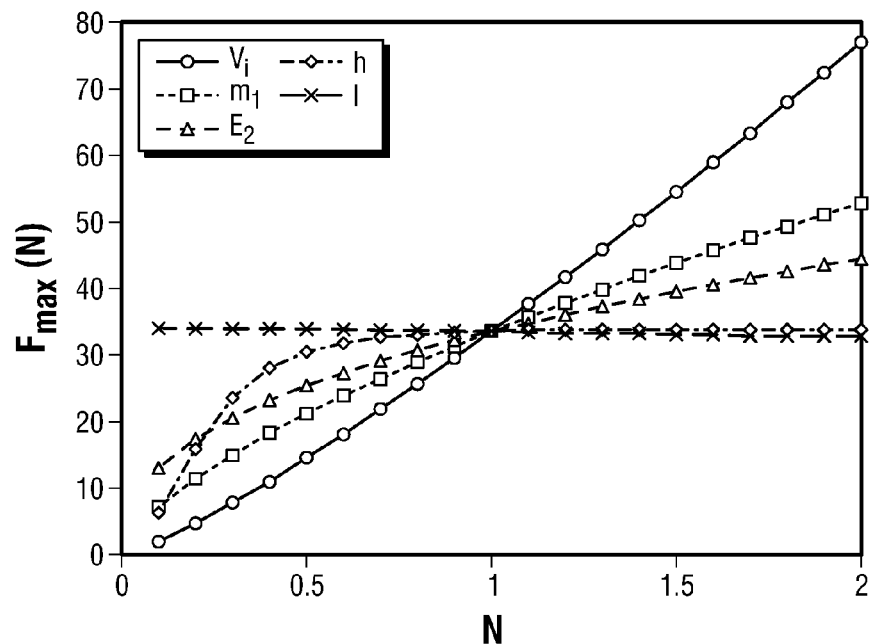
FIGS. 11 to 14 show respective sensitivity plots of influencing factors on maximum impact force, impact duration, maximum contact deformation and flexural energy loss.
Figure 12:
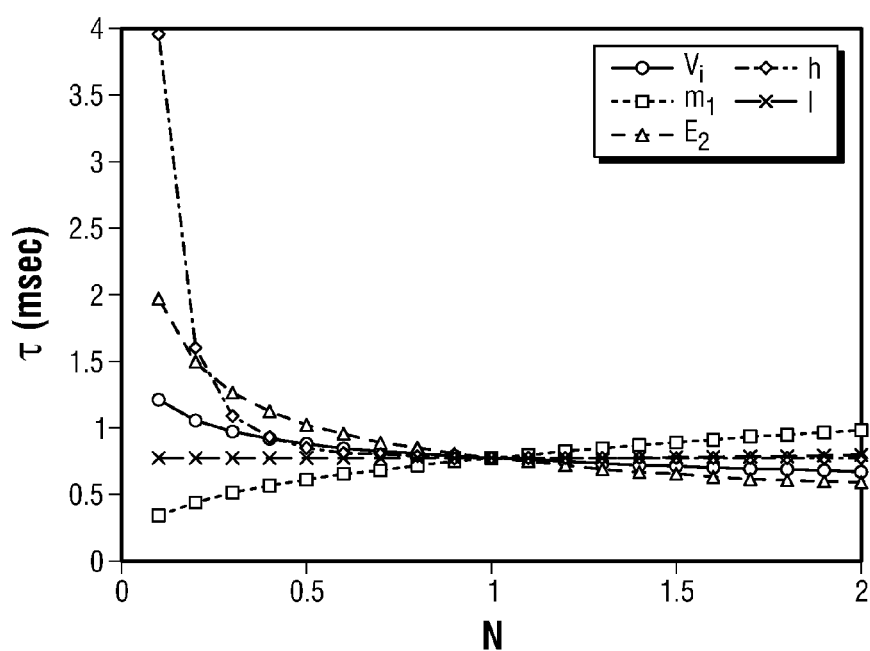
Figure 13:
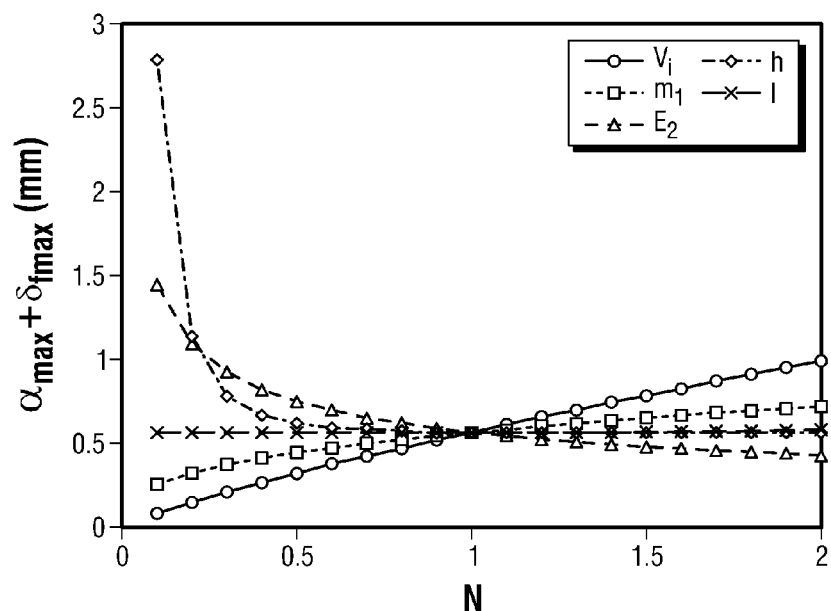
Figure 14:
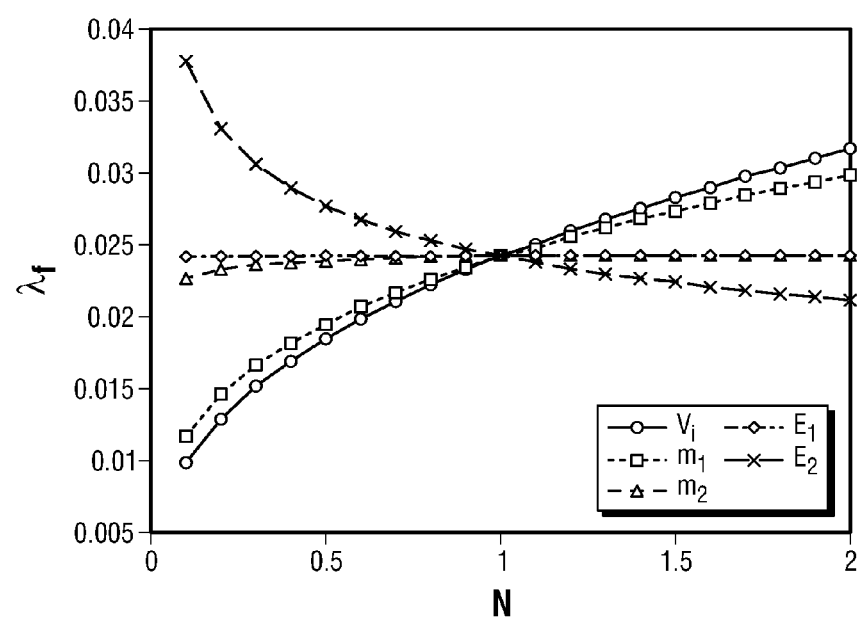

To compare the sensitivity between the two abnormality parameters, it can be observed from the plots that the effect of depth h is much more dominant than the effect of length l for N=0~1 (equivalent to h=0~25.4 mm, l=0~25.4 mm). However, when N=1~2 (equivalent to h=25.4~50.8 mm, l=25.4~50.8 mm), the two parameters have comparatively subtle influences on the observed quantities. This trend implies a sensitive range for the discriminators to sense the existence of an abnormality, irregularity or variance (as further discussed herein). Also, the length l is shown as being less significant when compared to all the other plotted factors for the first three dynamic quantities $F_{max}$, $\tau$ and $\alpha_{max} + \delta_{max}$ as shown in FIGS. 11, 12 and 13.

Figure 15:
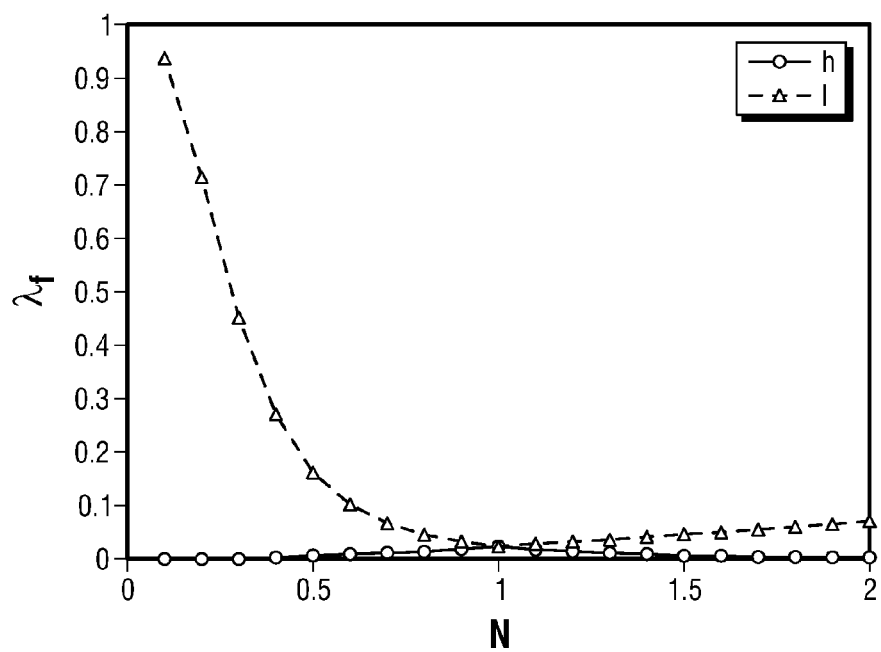
FIG. 15 shows an exemplary sensitivity analysis plot of irregularity dimensional quantities on flexural energy loss.

Yet the flexural energy loss percentage $\lambda_f$ presents much higher sensitivity to variation in both the depth h and the length l. It can be shown that $\lambda_f$ increases about 4.6% by doubling the abnormality length l, which is much higher compared to 0.74% by doubling the impact velocity $V_i$. Due to this difference in the variation range between the first five parameters ($V_i$, $m_1$, $m_2$, $E_1$, $E_2$) and the two abnormality parameters (h, l), the sensitivity plots were separated in FIGS. 14 and 15. As $\lambda_f$ is approaching the maximum value 1, the anomaly is getting closer to the impacted surface. As $\lambda_f$ decreases rapidly, the anomaly goes deeper. Alternatively, with the increase in the anomaly length l, $\lambda_f$ rises at a relatively stable rate. This phenomenon reflects more energy lost due to flexural vibrations induced by the growing anomaly.

Impact Acoustic Signal Analysis

The impact acoustic signal includes two parts: one is the impact force signal that can be measured by using a load cell as the impact tip. Another is the resultant acoustic signal recorded by a microphone. According to the contact dynamics model disclosed herein, the dynamic quantities are verified as being sensitive to the existence of an internal anomaly in a rubber structure.

The experimental impact force signal provides direct measurements of peak impact force and impact duration. These two quantities can be theoretically derived from the contact dynamics model. It is necessary to compare the experimental and theoretical derived quantities in order to validate the model. Also, the effects of a crack on the quantities are analyzed to verify the rationality of adopting these two quantities as anomaly discriminators. Analysis was performed in order to learn the effect of an internal anomaly on these two dynamic quantities.

Example

Rubber samples were prepared with the exemplary cubic shape and made of rubber with material properties as listed previously in Table 1. Two sets of block dimensions were used to study the effects of block length on the impact dynamics quantities:

50.8 mm×279.4 mm×101.6 mm (the "101.6 mm block"); and 50.8 mm×279.4 mm×152.4 mm (the "152.4 mm block").

Four samples of each dimension were fabricated, including one integral block and three blocks each having an aperture incorporated at top and bottom extents thereof.

Given three different depths of h as 25.4 mm, 19.05 mm, 12.7 mm and two lengths l as 25.4 mm and 50.8 mm, the three blocks with apertures were analyzed. The closest distance between top and bottom apertures was 228.6 mm, which was obtained by deducting two depths h of 25.4 mm from the overall height of the block. It was proven previously that impact dynamics discriminators become insensitive to anomalies deeper than 25.4 mm, and correspondingly it can be assumed that far-field variations (such as another anomaly located at 228.6 mm away from the affected zone of the applied impact) can be ignored.

Figure 16:
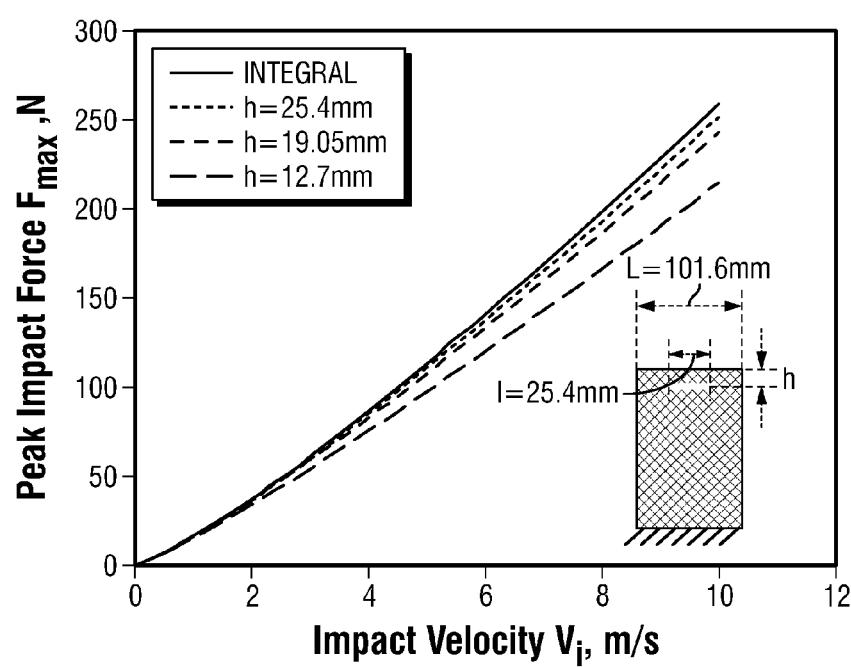
FIGS. 16 and 17 show exemplary relationships of theoretical peak impact force and theoretical impact duration, respectively, versus impact velocity for rubber blocks with an embedded anomaly having varying depths.
Figure 17:
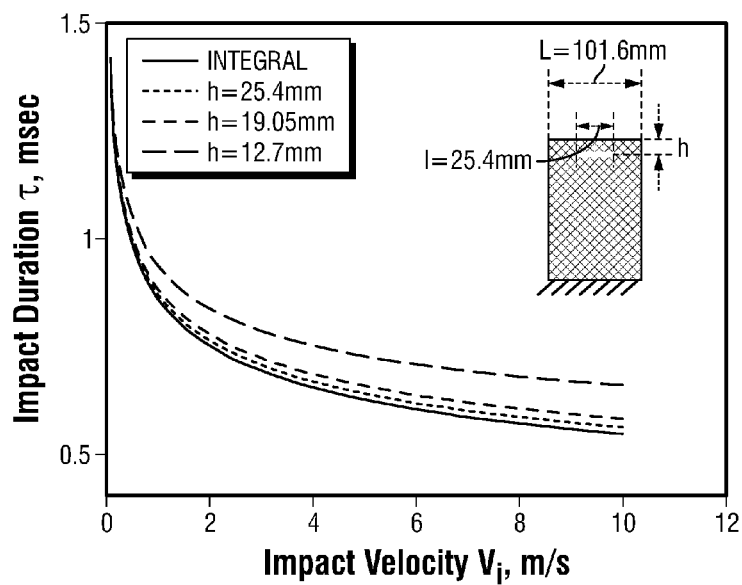

Theoretical values of peak impact force $F_{max}$ and impact duration τ are calculated based upon the developed integral model and the anomaly model, for four scenarios in the 101.6 mm rubber block. $F_{max}$ and τ were plotted against the impact velocities in FIGS. 16 and 17, respectively. At higher velocities, the model predicts higher impact force and lower impact duration for each scenario. For a certain impact velocity, the integral block (curve 1) gives a higher impact force and lower impact duration than the aperture blocks (curve 2,3,4), which is associated with additional membrane bending deflection introduced by the embedded anomaly rather than local contact deformation. By approaching the predicted value for the integral model, it is also observed that the peak impact force increases while the impact duration decreases with growing depth of an embedded anomaly. The trend shows that the deeper the anomaly is located, the less effect the existence of the anomaly has on the predicted discriminators. This validates the rationality of fabricating two apertures (i.e., "anomalies") in a single block for simulating the two shoulders in a tire casing.

Figure 18:
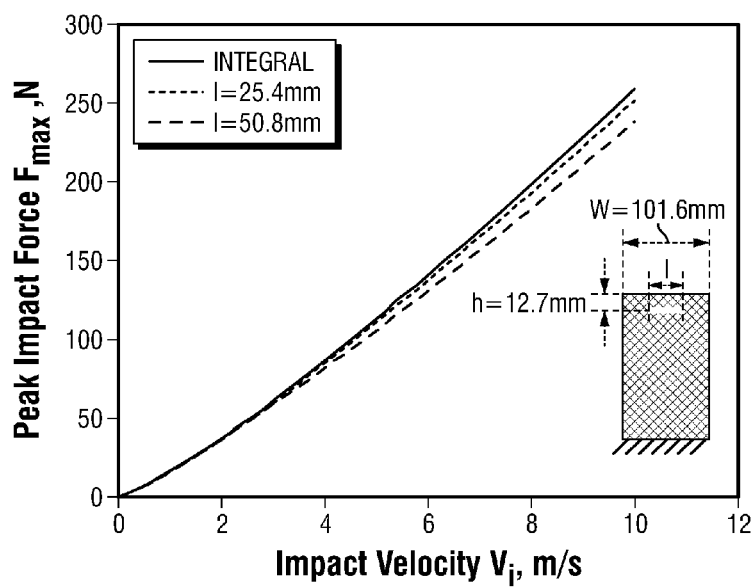
FIGS. 18 and 19 show exemplary relationships of theoretical peak impact force and impact duration, respectively, versus impact velocity for rubber blocks with an embedded anomaly having varying lengths.
Figure 19:
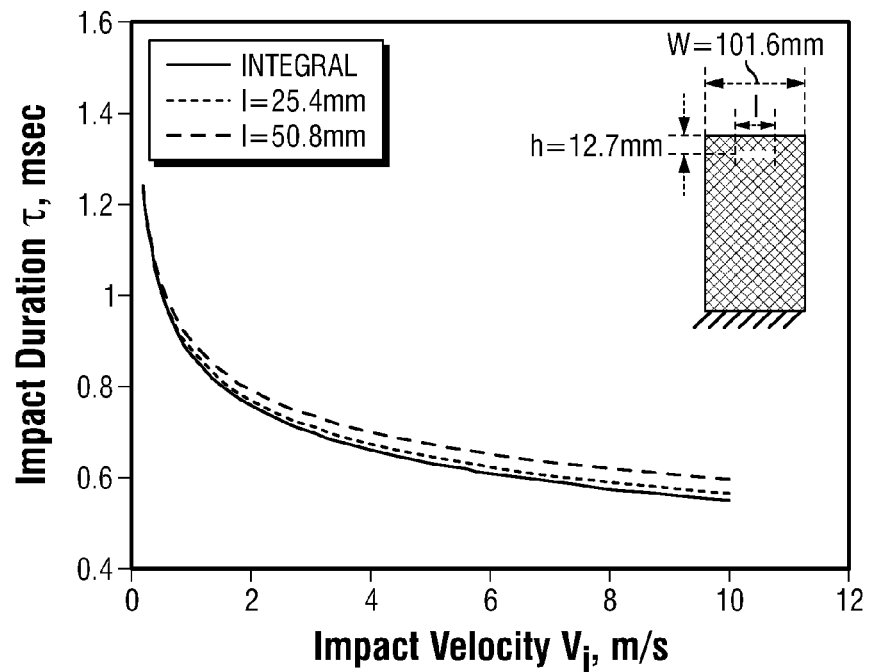

FIGS. 18 and 19 show the varying tendency of peak impact force and impact duration resulting from impact velocity for three scenarios (i.e., the 101.6 mm integral block and two apertured 101.6 mm blocks) with respective anomaly lengths of 25.4 mm and 50.8 mm at a common depth of 12.7 mm. For a given impact velocity, the apertured blocks present lower impact force and longer impact duration than the integral block. Thus, the narrower the anomaly is, the less difference there is in the discriminators between the integral and aperture cases. It is straightforward that a block with an anomaly length infinitely approaching zero is identical to an integral block. It can be inferred simultaneously that the impact dynamics discriminators can be incapable of detecting anomalies that are too small in size.

Therefore, the capability of the impact dynamic quantities in anomaly inspection relies on the sensitivity and detectable range of the sensors. It may also be concluded that when the anomaly is located deeper than 25 mm, the anomaly may not be detected by looking for change in the measured peak impact force. The peak impact force, however, can be used as a discriminator to differentiate anomaly depths. Therefore, the targeted belt edge anomaly in the tire shoulder as discussed herein is always less than 25.4 mm.

Figure 20:
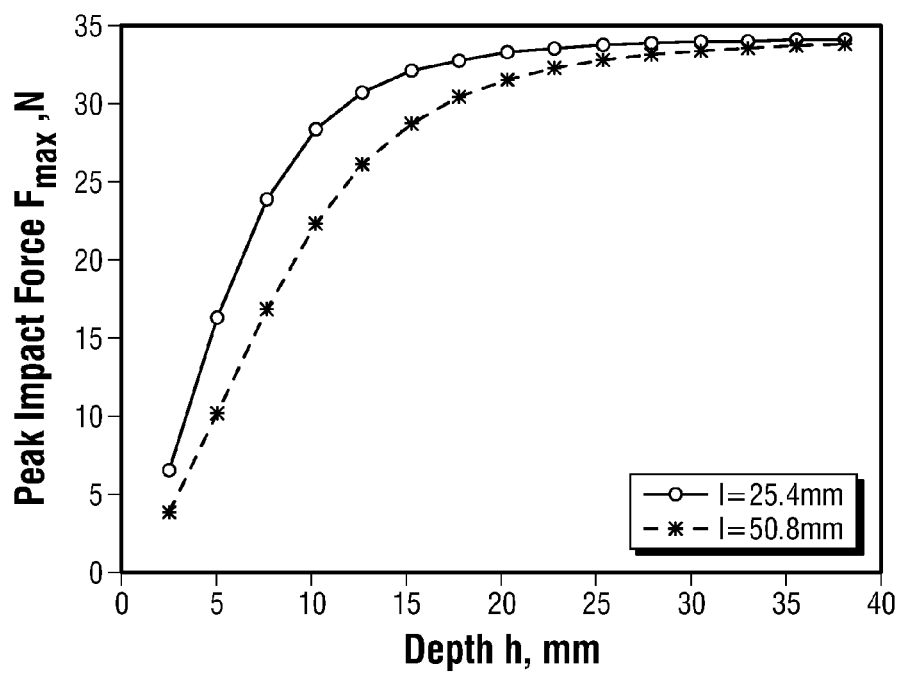
FIGS. 20 and 21 show predicted peak impact force and predicted impact duration versus depth of an anomaly, respectively.
Figure 21:
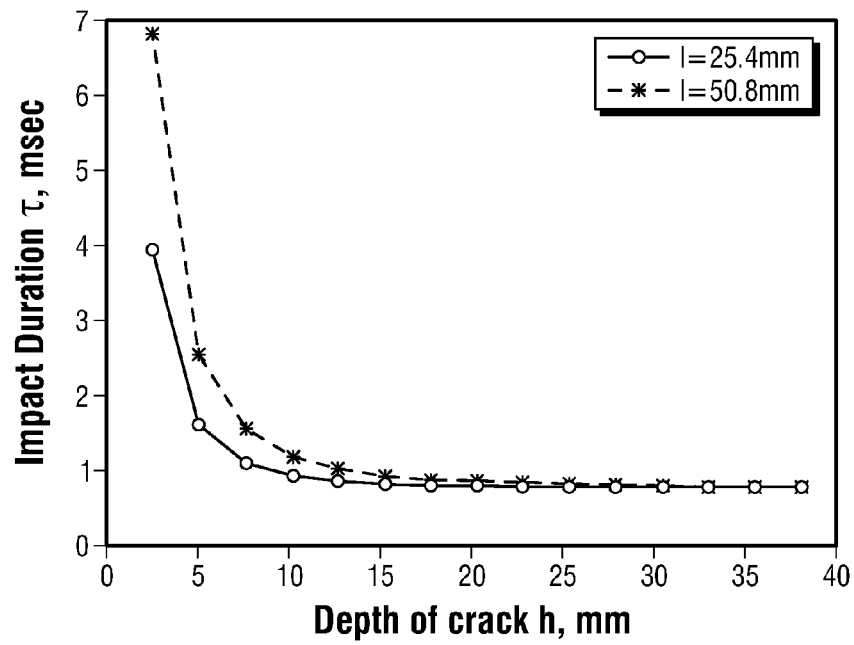

In FIGS. 20 and 21, $F_{max}$ and τ, respectively, are theoretically derived for 101.6 mm blocks with an anomaly of varying depth, considering an impact velocity at 1.85 m/s. Two scenarios are compared between an anomaly of length l=25.4 mm and an anomaly of length l=50.8 mm. For shallower anomalies at a depth less than 25 mm, the impact force increases more rapidly with the increase in anomaly depth than for deeper anomalies. This phenomenon indicates that the impact force can be a very sensitive discriminator for anomalies close to the impacted surface, yet it may be more difficult to distinguish anomalies at different depths when they are deeper in the structure.

Figure 22:
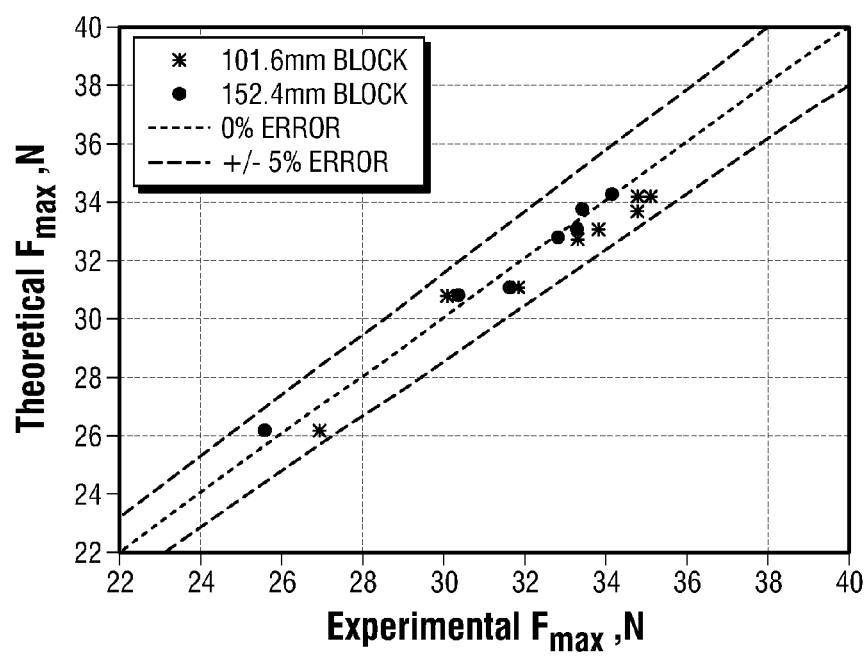
FIGS. 22 and 23 show exemplary comparisons of peak impact force and impact duration, respectively, that are theoretically predicted and experimentally obtained.

FIG. 22 compares the peak impact force $F_{max}$ that is theoretically predicted and experimentally obtained. Very good coherence is shown between the predicted and experimental $F_{max}$, where all the plotted points in the figure fall within 5% error margins. This correlation enables the prediction of impact force measured from a rubber composite structure and anomaly identification based upon the measured peak impact force.

Figure 23:
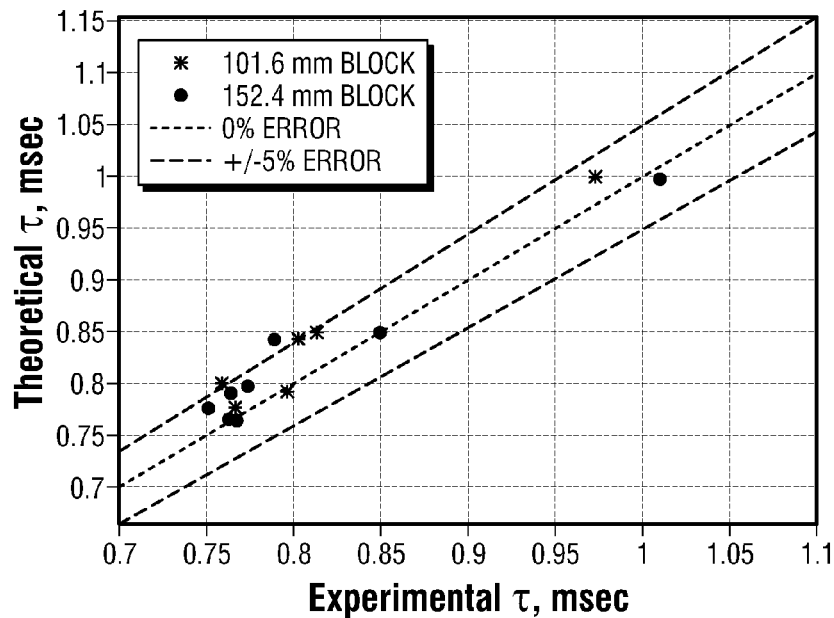

FIG. 23 shows the correlation between the predicted and the experimental impact duration, where the majority of the measurements fall in a relatively small range from 0.75 to 0.85 msec. The two measurements "out of the crowd" are taken from two samples having anomalies with the longest comparative transverse length and lowest depth. This phenomenon suggests that impact duration can be a good discriminator for a very severe anomaly. For an anomaly that is relatively small and deep, however, impact duration measured for an irregular or varied structure may not provide a clear distinction from that measured for a structure having structural integrity.

It can be concluded that there is a detectable or sensitive range while using peak impact force and impact duration as anomaly discriminators. Alternatively, it means that anomalies that are deep or narrow may not be readily discerned by certain contact dynamics discriminators ($F_{max}$ and τ). With the knowledge of a specific set of input parameters for the presently disclosed impact acoustic method (e.g., including, but not limited to, impact velocity and the impactor's material properties), a detectable range of the embedded anomaly can be determined.

Theoretical Analysis of Acoustic Signal

Figure 24A:
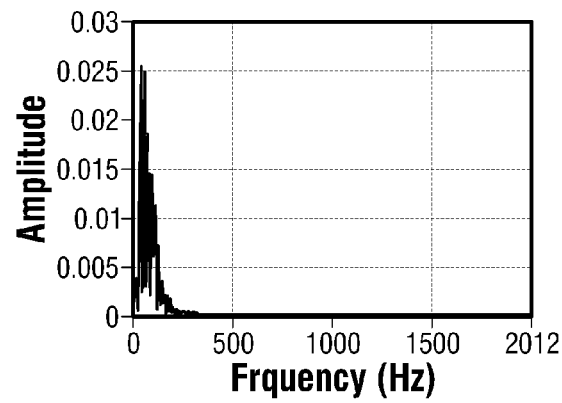
FIGS. 24A and 24B show exemplary effects of impact velocity on frequency coverage.
Figure 24B:
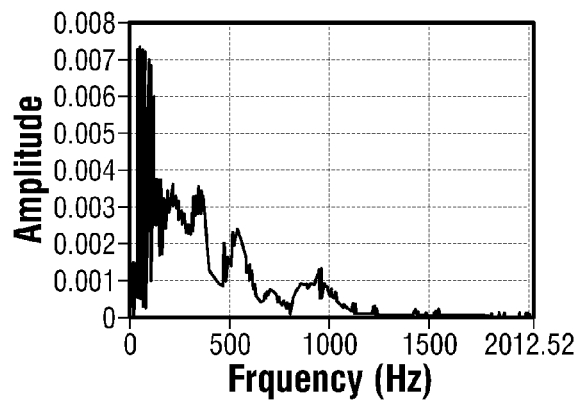
Figure 25A:
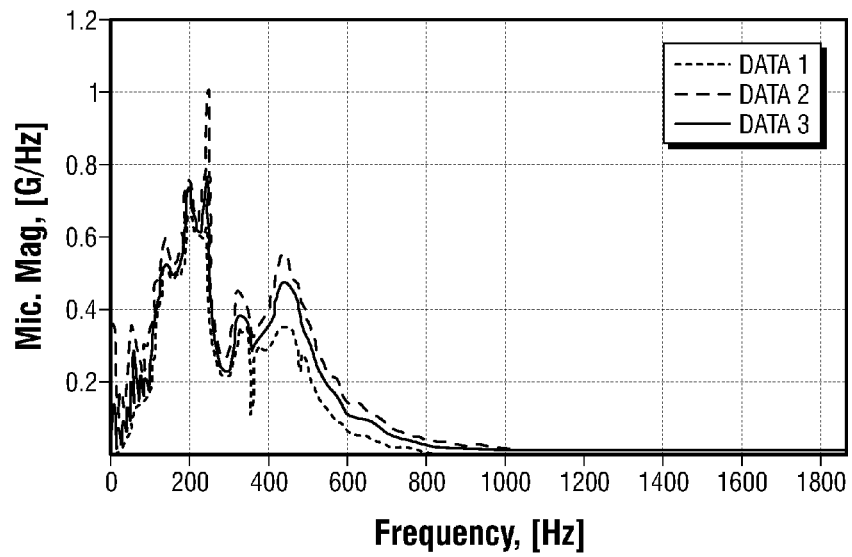
FIGS. 25A and 25B show exemplary effects of impactor mass on frequency coverage.
Figure 25B:
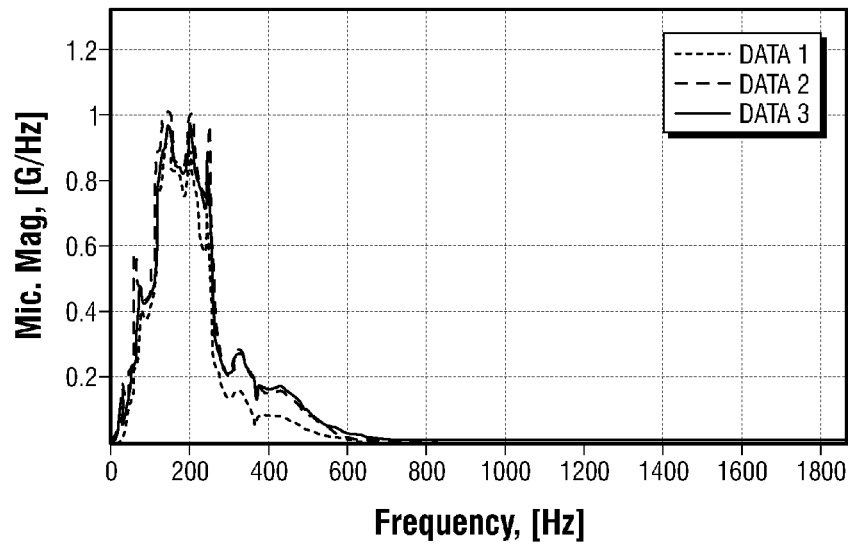

It has been investigated earlier through the contact dynamics model that impact velocity and the impactor's mass have phenomenal effects on the duration of impact, which in turn controls the excitable range of frequency components. Experimental studies are performed for both parameters, and the frequency spectrums are compared between two scenarios for each observing parameter. FIGS. 24A and 24B compare the effects of impact velocity on frequency coverage, while FIGS. 25A and 25B illustrate the effects of the impactor's mass on the corresponding bandwidth. The figures indicate that the frequency coverage is larger for higher impact velocity and lower impactor mass, which matches the theoretical conclusions made previously. Consequently, selection of proper impact velocity and impactor mass affects the success of the impact acoustic signal in the frequency domain analysis.

The microphone gain is usually not a constant value at lower audible frequency range (20-200 Hz). If the impact acoustic signal contains a large amount of low audible frequency contents, the time-domain amplitudes are a distorted proportional reproduction of the velocity. Accordingly, the initial contact sound wave amplitude can be estimated as proportional to the velocity of vibration in the impacted solid. Furthermore, it can be derived that the area under the initial contact sound waveform is proportional to the maximum deformation generated by the impact while assuming the displacement to voltage gain is constant over time. The free vibration stage of the acoustic signal is an indirect measurement of the surface movements after the contact. Therefore, the ringing sound amplitudes are dependent on the initial position of the structure at the beginning of free vibration. This initial condition can be assumed as the maximum deformation. The maximum deformation subjected to the impact at the end of the contact duration was analyzed in the contact dynamics model as related to the existence of an internal anomaly.

Figure 26:
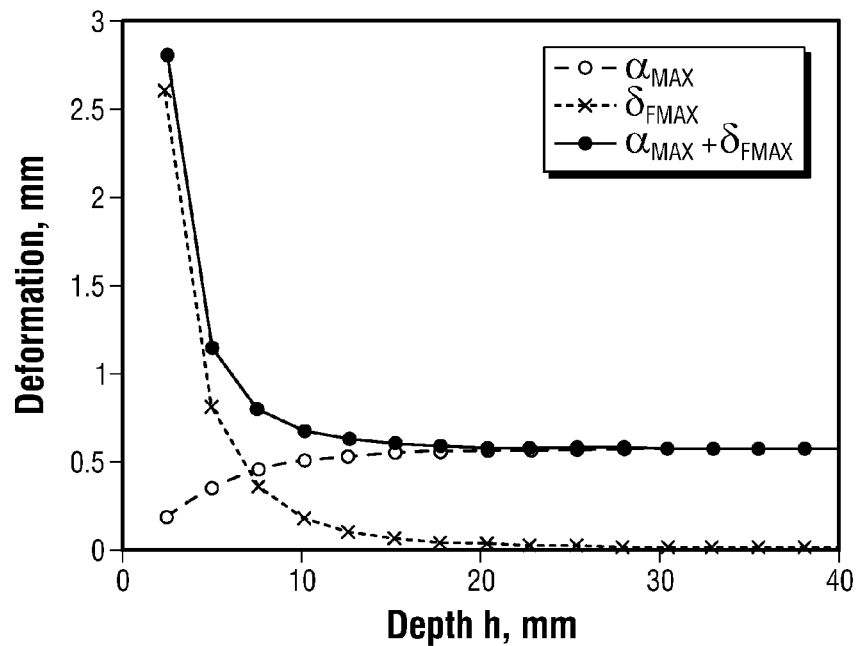
FIG. 26 shows predicted maximum deformation versus anomaly depth.

The relationship between the maximum deformation $d_{max}$ and the anomaly dimensions can be theoretically derived based on the developed anomaly model as shown in FIG. 26. Contact deformation $\alpha_{max}$ and bending deformation $\delta_{fmax}$ vary with respect to increasing anomaly depth. Overall, the total maximum deformation decreases with an increase in the anomaly depth, which indicates that $d_{max}$ increases with the presence of an internal irregularity (e.g., one or more cracks). This relationship is less significant when the irregularity is located deeper than around 20 mm, suggesting that this dynamic quantity is also limited to reveal irregularities within a certain detectable range.

The fundamental basis of frequency-domain analysis is that an anomaly or irregularity usually lowers the structural stiffness k, thus resulting in lower resonant frequencies w. The defective structural mass considered in an impact-acoustic method can be assumed as a portion of rubber above an anomaly (e.g., a crack). In the case of a defective specimen, m is decreased. In this case, natural frequency is w=(k/m)^0.5 by decreasing m. The resonant frequency ω generated by vibration of m above the anomaly will increase and therefore yield many higher frequency components. Correspondingly, it results in richer frequency components at higher frequency bandwidth of the acoustic signal. The total impact energy transformed into the structure is partially dissipated by flexural bending deformation caused by the internal anomaly. It may therefore be more efficient to distinguish vibrations due to local contact deformation at lower frequencies from flexural vibrations at higher frequencies in the power spectrum of the acoustic signal. Flexural vibration energies are directly related to the initial maximum deflection $\delta_{fmax}$ caused by the impact, while the amount of resonant vibration energies can be attributed to the magnitude of the local contact deformation $\alpha_{max}$.

The amount of energy in an acoustic spectrum reflects both stages of the impact's acoustic responses: the initial contact stage and the free vibration stage. The flexural energy loss factor is a theoretical quantity that measures the percentage of energy lost by the flexural bending deformation. This flexural energy loss can be alternatively understood as contributing to the decrease in the structural stiffness. The bending stiffness of the materials above the internal anomaly $K_f$ is a function of anomaly depth and length (recalling that in increase in h and a decrease in l both reduce $K_f$). Thus, the bending stiffness decreases from infinite for an integral structure to a finite value for an irregular structure (i.e., one having at least one anomaly), and reduces with the growing severity of the internal crack. Therefore the energy loss factor can be estimated as an alternative measurement of increased higher frequency components.

Experimental Validation of Acoustic Time-Domain Discriminators

In the time-domain of the acoustic signal, two accumulated areas $A_1$ and $A_2$ were demonstrated as experimental interpretations of the maximum deformation $d_{max}$ and can thus be adopted as anomaly discriminators. Experimental validation on the effects of an internal anomaly on $A_1$ is given by applying impact acoustic testing on the artificial rubber samples as disclosed herein.

Figure 27:
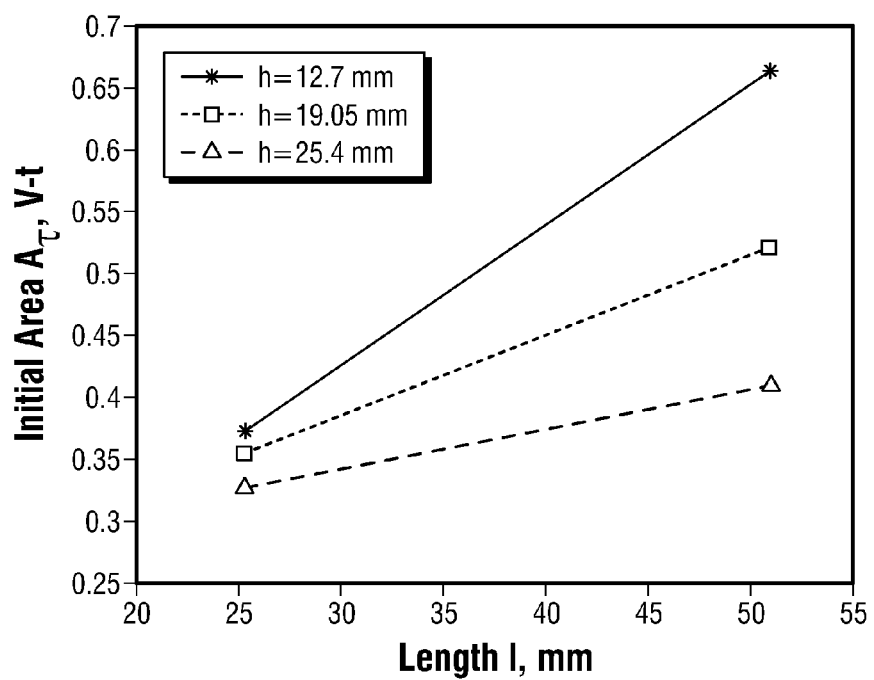
FIG. 27 shows an exemplary sound waveform attribute $A_1$ versus anomaly length.

One experimental quantity that equivalently measures the maximum deformation is the initial area of the acoustic time signal $A_1$. FIG. 27 shows the experimental attribute $A_1$ plotted against the anomaly length for three different anomaly depths. As shown, acoustic time signal $A_1$ correlates with the anomaly dimensions as the theoretical quantity $d_{max}$ does, and it can be adopted to reveal the presence of internal anomalies in rubber structures.

Figure 28:
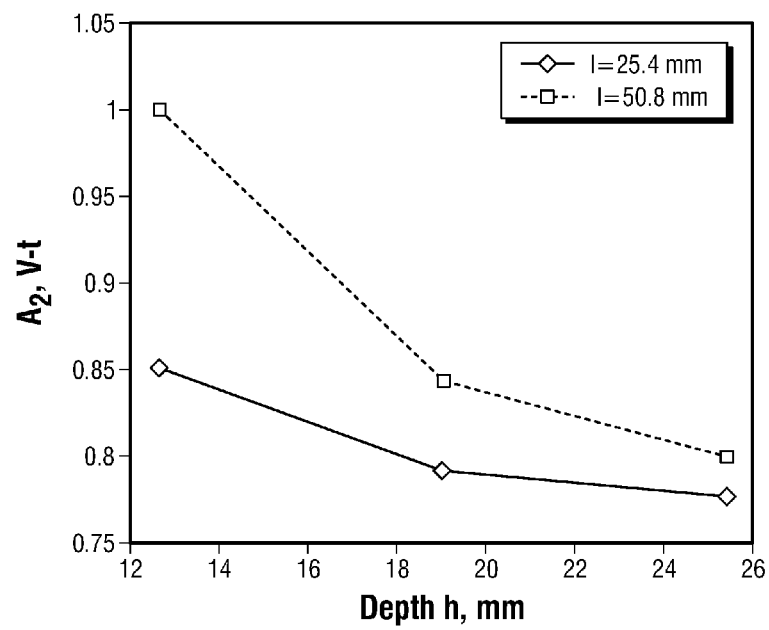
FIG. 28 shows an exemplary accumulated ringing sound area $A_2$ versus anomaly depth.

Accumulated areas $A_2$ calculated from the ringing sound waves are plotted against the crack depth in FIG. 28. It is shown that increased severity of an internal anomaly produces higher $A_2$, which matches the predicted trend of $d_{max}$. The two features $A_1$ and $A_2$ calculated from the time-domain acoustic waveform are therefore both discriminators for internal anomalies and irregularities in rubber structures.

Experimental Validation of Acoustic Frequency-Domain Discriminators

It was observed directly that spectral energy lower than 640 Hz is higher for the integral than the two irregular structures (i.e., those having one or more anomalies), and becomes lower when the crack gets closer to the surface. Accordingly, the spectral energy higher than 640 Hz (attributed to flexural vibrations) is higher for irregular structures due to the flexural vibrations introduced by the internal delamination. The relationship of the power spectral energy below or above 640 Hz matches the trend of $\alpha_{max}$ and $\delta_{fmax}$ respectively, which in turn indicates that the effect of an internal anomaly on impact acoustic responses can be identified through manipulation of spectral energies. Either the local peak amplitudes or accumulated spectral densities can be regarded as discriminators for anomaly identification.

The shifts in modal frequencies are attributed to the flexural vibration of irregular structures. They can also be related to the energy distribution ratio of the resonance to the overall vibration energy. The accumulative power ratio is defined for this purpose to examine energy distribution of an interested frequency range.

The power spectrums are experimentally acquired from an integral rubber block sample and three irregular samples with anomalies at depths of 12.7 mm, 19.05 mm and 25.4 mm, respectively. Each power spectral density is normalized to its corresponding maximum density in each plot. In comparison, the power density at higher frequencies (above 500 Hz) becomes greater from the integral block to the shallowest cracked block.

Furthermore, a term ΔPR is defined as the difference of power ratio values of the apertured scenario from the integral measurement:

$$\Delta PR = \Delta PR_{integral} - \Delta PR_{cracked}.$$

Figure 29:
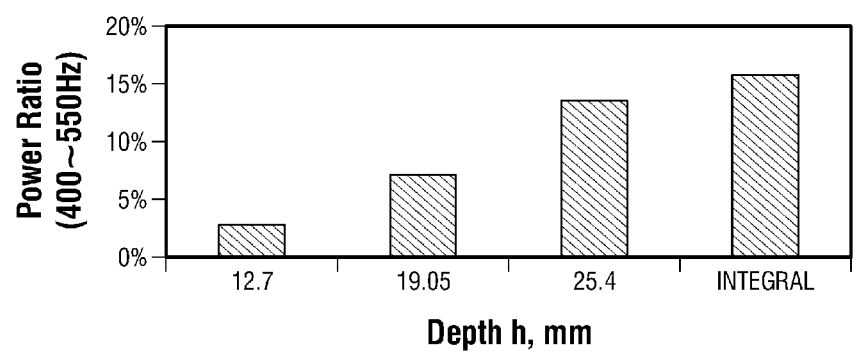
FIG. 29 shows an exemplary measured power ratio value versus anomaly depth.
Figure 30:
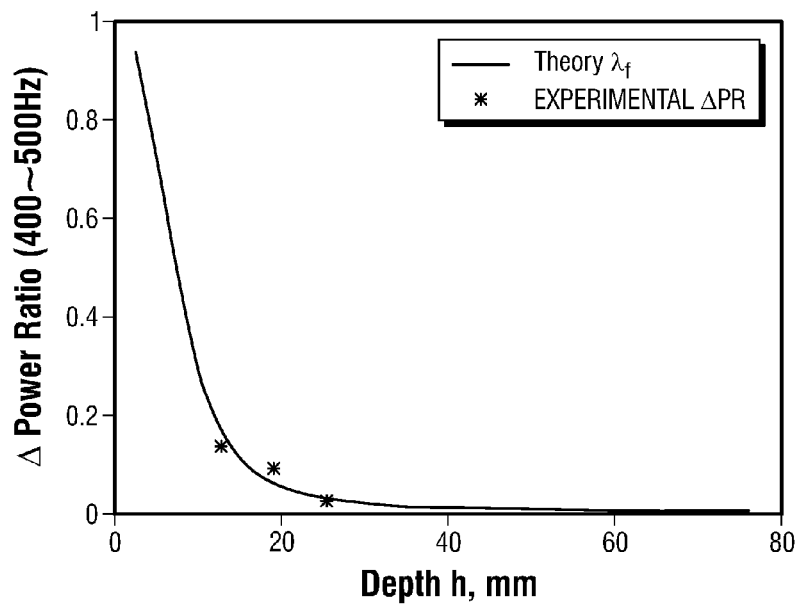
FIG. 30 shows an exemplary comparison of theoretical calculated flexural energy loss and experimentally measured power ratio.

The experimentally measured discriminator ΔPR is identical to the theoretically predicted $\lambda_f$, both of which indicate the anomaly status of the structure:

The power ratio values are calculated by taking the ratio of accumulated densities in the frequency range between 400 and 550 Hz to those in the overall frequency coverage (0~3000 Hz). The results are presented in FIG. 29. Values of ΔPR for the three irregular blocks are then calculated and compared to a theoretical curve for $\lambda_f$ versus anomaly depth (see FIG. 30). The comparison shows favorable accordance between the experimental discriminator ΔPR and the theoretically estimated flexural energy loss factor $\lambda_f$.

Implementation of the Impact Acoustic Method

The presently disclosed impact acoustic method may be implemented on used tires (including used truck tires) for the purpose of examining used tire casings and determining the integrity thereof. As disclosed herein, there are seven discriminators verified as feasible for inner crack identification: peak impact force, impact duration, area under initial contact sound, free vibration energy, accumulative power ratio, power spectrum local peak magnitude and accumulated spectral energy (see Table 4 below).

TABLE 4

Summary of Discriminators of Impact-Acoustic Anomaly Identification

| Experimental Measurements | Experimental Discriminators | | Analytical Contact of Dynamics Quantities | |
|---|---|---|---|---|
| Force-time | Peak impact force | $F_{max}$ | Peak impact force | $F_{max}$ |
|  | Impact duration | τ | Impact duration | τ |

TABLE 4-continued

Summary of Discriminators of Impact-Acoustic Anomaly Identification

| Experimental Measurements | Experimental Discriminators | | Analytical Contact of Dynamics Quantities | |
|---|---|---|---|---|
| Sound-time | Area under initial peak | $A_1$ | Maximum deformation | $d_{max}$ |
| | Area under ringing sound | $A_2$ | Maximum deformation | $d_{max}$ |
| Sound-frequency | Accumulative power ratio | $PR_i$ | Flexural energy loss factor | $\lambda_f$ |
| | Local peak spectral density at higher frequency bandwidth | $P_f$ | | |
| | Accumulative spectral energy at higher frequency bandwidth | $E_f$ | | |

$F_{max}$ and $\tau$ can be measured directly from a force-time signal and can also be calculated from a sound-time signal.

Table 5 indicates how the predicted dynamic quantities change for increasing anomaly depth and length. It has been validated by testing cubic rubber samples with artificial anomalies that the experimentally measured discriminators compare favorably with the corresponding analytical dynamic quantities. For example, lower $F_{max}$ and higher flexural energy $E_f$ can be measured in a structure having anomalies as compared to an integral structure.

TABLE 5

Effect of Anomaly Dimensions on Chosen Parameters

| Analytical | Direction of Change | | |
|---|---|---|---|
| Dynamic Quantities | Depth of crack h increased from 0 | Length of crack l increased from 0 | Experimental Discriminators |
| $F_{max}$ | Increase | Decrease | $F_{max}$ |
| T | Decrease | Increase | T |
| $d_{max}$ | Decrease | Increase | $A_1, A_2$ |
| $\lambda_f$ | Decrease | Increase | $PR_i, P_f, E_f$ |

Experimental Setup and Instrumentation

In the experimental stage, used radial truck tires of three different belt constructions were tested by impact-acoustic method. The treads were buffed off for all of the samples to ensure uniform quantity of materials circumferentially and eliminate the effect of tread design variances. The focused area of anomaly examination is the belt edge separation at both shoulders of a tire casing. The separation between the belt edge and the surrounding rubber materials usually predicts the initiation of severe tire failures, which lays parallel along the belt direction. The anomalies can propagate into the belted regions in the undertread area resulting in catastrophic tread separations.

Figure 31:
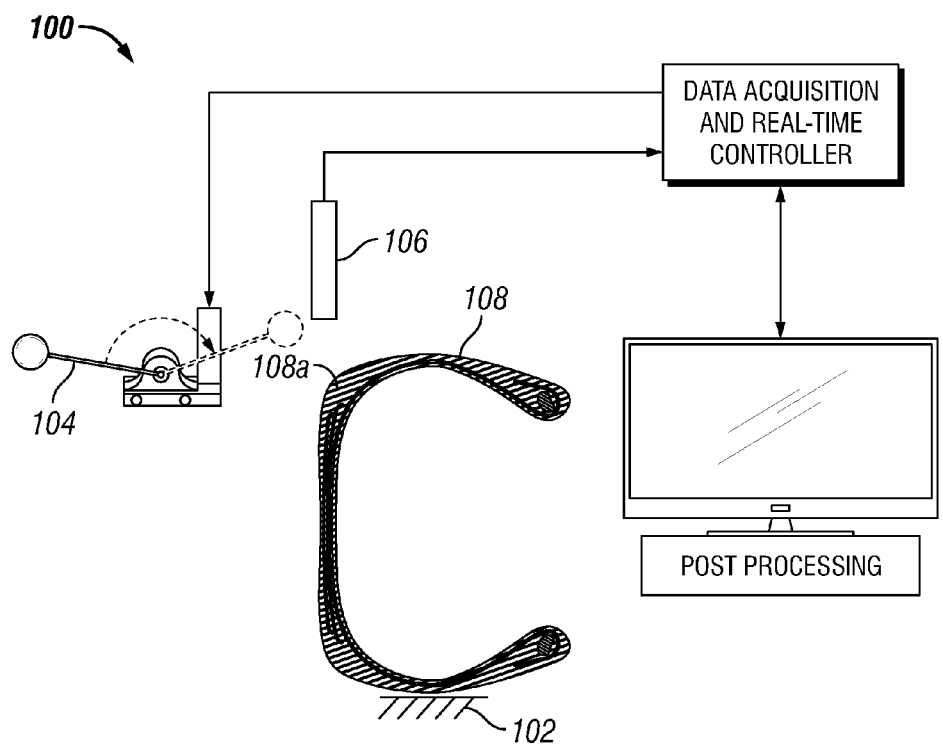
FIG. 31 shows an exemplary tire anomaly detection system that employs an exemplary impact-acoustic method as presently disclosed.

Referring further to FIG. 31, an exemplary tire anomaly detection system 100 is provided that generally includes a tire support system and an impact system. The tire support system may include a test platform 102. One or more test platforms may be designed to satisfy complete automation for these systems (e.g., the tire support system may incorporate a tire rotation system). Manual operations may be performed for one or more auxiliary subsystems (e.g., loading/unloading system, tire-centering systems, positioning system, etc.).

An exemplary impact system includes a motor-driven impactor 104 and an acoustic transducer such as a microphone 106 placed adjacent to a targeted area of a tire casing 108. For example, a targeted area may be a shoulder 108a of tire casing 108, and microphone 106 may be disposed a fixed distance therefrom. Tire casing 108 may be comparable to tire casing 12 as shown in FIG. 2. It is understood that the impactor may be an impactor that generates an input pressure wave. Impactor 104 may therefore be actuated by a solenoid, by a manual input or by any other amenable actuation means as known in the art.

Microphone 106 may be either moved along with impactor 104 or independently with three degrees of freedom as desired. Impactor 104 may have a miniature size and low mass load cell designed to measure dynamic forces over a ±50 g dynamic range scale over a wide frequency range, quasi-static to 50 kHz. Microphone 106 includes other sensors of the impact-acoustic system with a range of 70 Hz-20 kHz.

Tire casing 108 is placed on test platform 102 and centered thereon. In an embodiment, impactor 104 has a miniature size and low mass (e.g., at or about 4.5 g) IEPE force sensor designed to measure dynamic forces over a ±222N dynamic range scale, with sensitivity of 22.5 mV/N. A DC motor driving impactor 104 can reach a maximum speed with maximum efficiency at 8170 r/min (i.e., approximately 0.98 m/s for the 2.3 mm rotor). Therefore, impactor 104 provided at an extent of a 50 mm shaft can reach a maximum impact velocity at around 40 m/s. In some embodiments, microphone 106 may be an electret condenser microphone that receives signal from a single direction covering acoustic frequency from 70 Hz up to 20 kHz.

Figure 32:
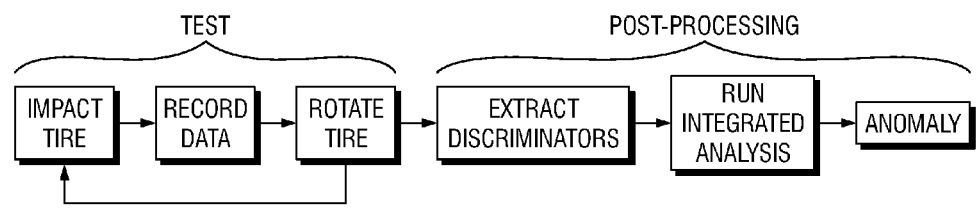
FIG. 32 shows a flowchart for an exemplary testing algorithm as disclosed herein.

A flowchart for an exemplary testing algorithm that controls the hardware and checks for internal anomalies (including data collection and post-processing) is shown in FIG. 32. Complete impact acoustic tests are performed circumferentially on both shoulders of the tire casing with desired resolution controlled by the rotation stepper motor. The algorithm as illustrated is divided into two parts: one to control the hardware and to record data, and the second to extract the anomaly indicators and to feed them into the stochastic algorithm involving an ANN.

Figure 33:
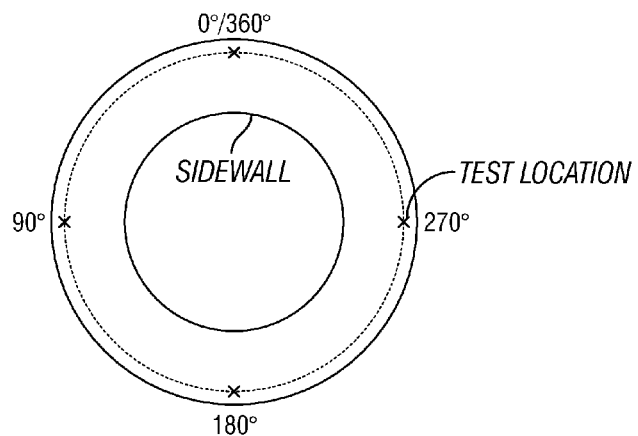
FIG. 33 shows a plan view of a test tire indicating exemplary test line and locations.

A minimal resolution of 0.9° can be achieved by running the motor under half step mode. Test resolution is chosen as 3.6°, which discretizes the circumference of the test line into 100 segments, as seen in FIG. 33. After each impact and signal recording, the tire is rotated 3.6° toward the next test location until the entire circumference gets covered. The starting location of the test line, marked as 0° or 360°, is measured with two repetitions.

For accuracy of the collected sound waveform, the minimum sampling frequency should be at least ten times of the highest frequency of interest. The sampling rate for acoustic signal acquisition is set as 41 kHz for this purpose. The total number of samples is set as $2^{14}$ (i.e., 16384), thus the total recording time of the acoustic signal is 0.4 seconds, yielding a frequency resolution of 5 Hz. The post-processing stage concludes discriminator extraction from both force and acoustic signals and further integrated analysis for anomaly identification.

Using the impact-acoustic test data, an NN algorithm was developed to interpret the measured indicators both from the time and frequency domains to predict an extent and location of internal anomalies. Although there are a variety of neural networks, a feed forward NN with a back propagation algorithm for supervised learning was used for preliminary tire anomaly evaluation. Basis rules were established as disclosed herein at least with reference to FIG. 4.

The post-processing of measurements includes three stages: extraction of discriminators, offline ANN training and online ANN evaluation. The discriminator quantities are computed based on the sound waves and the force signal. Based upon the selected database, those extracted discriminators are fed into the NN for offline training to generate the weight matrices that comprise the transfer function of the network. The most suitable weights for the selected database are saved for online evaluation of unknown tires.

Figure 34:
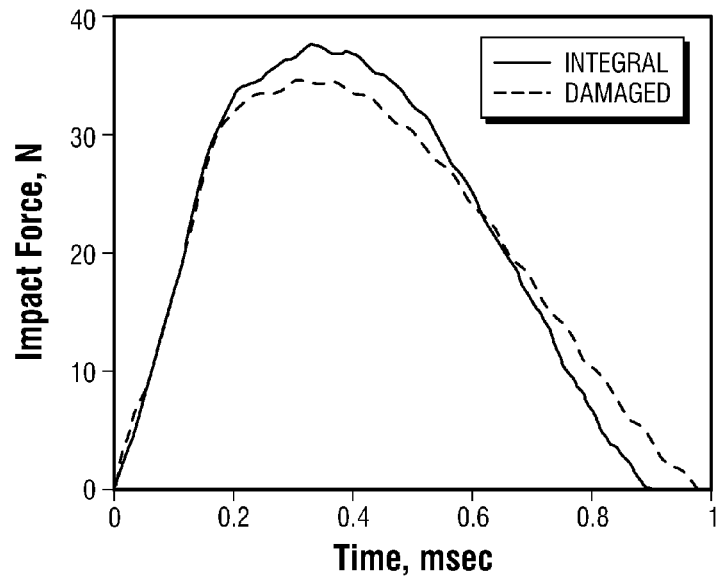
FIG. 34 shows exemplary time histories of impact forces measured from a sample tire.

Typical time histories of impact forces measured from a sample tire are shown in FIG. 34. Representative data is measured from corresponding positions on the tire, and these are selected from the integral and irregular areas, respectively, according to a corresponding shearography image. The solid force-time curve for the integral spot presents higher peak force and shorter contact duration than the dashed curve of the irregular spot (i.e., having an embedded anomaly). The results agree with the theoretical impact dynamics model, in which higher impact force and shorter impact duration were predicted for an integral structure.

Figure 35A:
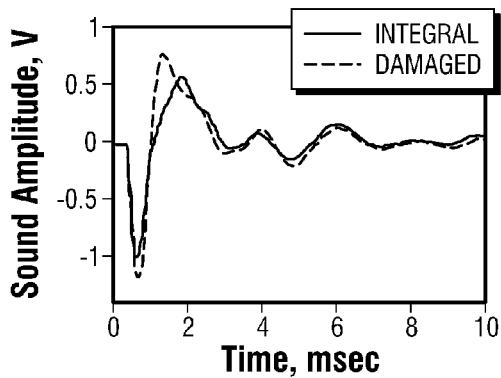
FIGS. 35A and 35B respectively show exemplary time histories and power spectrums of impact sound.
Figure 35B:
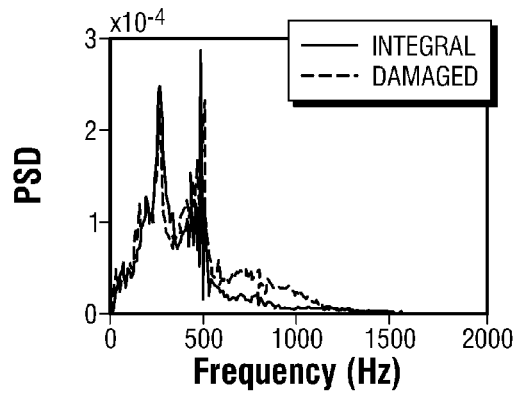

FIGS. 35A and 35B respectively show the typical time histories and the corresponding power spectrum of the impact sound measured from the same two spots as those in FIG. 34. It can be observed from the sound-time waveform that the area under the initial downward peak is smaller for the integral spot than the irregular one. The analysis of the frequency domain requires the knowledge of the resonant frequency subjected to the local contact deformation, which can be determined according to the impact duration that $f_c=1/(2\times0.9 \text{ msec})\approx555$ Hz. In the power spectrum, the spectral densities at frequency higher than 550 Hz are greater for the irregular curve, which indicates more flexural vibration energy due to the embedded anomaly. Accumulative power ratio PR (calculated for the higher frequency components ratio), peak flexural spectral $P_f$ and accumulated flexural energy $E_f$ can be taken as anomaly discriminators.

The flexural bending deformation can be smaller than the artificial irregular rubber sample, since the actual belt-edge anomaly in a tire structure usually presents a much smaller gap between two separated surfaces than the artificial anomaly made in the rubber samples. This mitigates the effect of the resonant frequency shift by reducing the variances in the structural stiffness.

Effect of Impact Location

Figure 36:
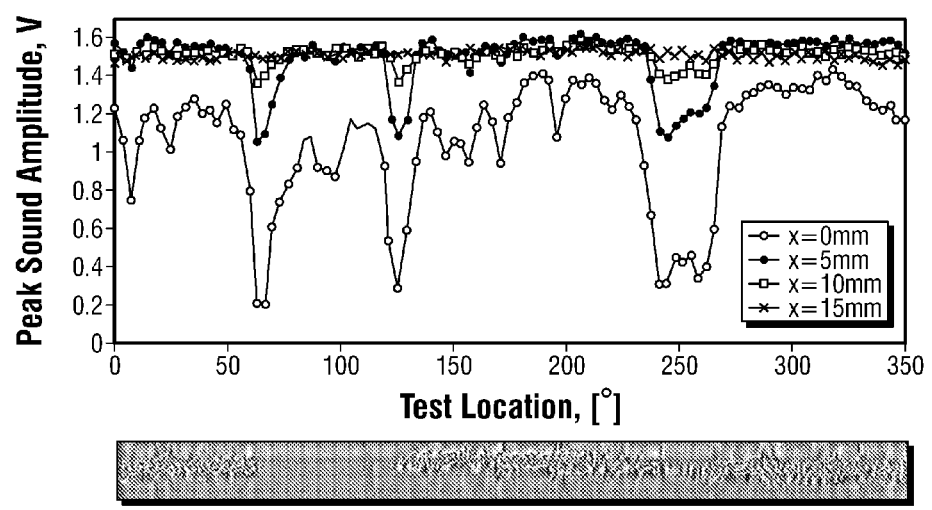
FIG. 36 shows the influence of impact location on peak sound amplitude.
Figure 37:
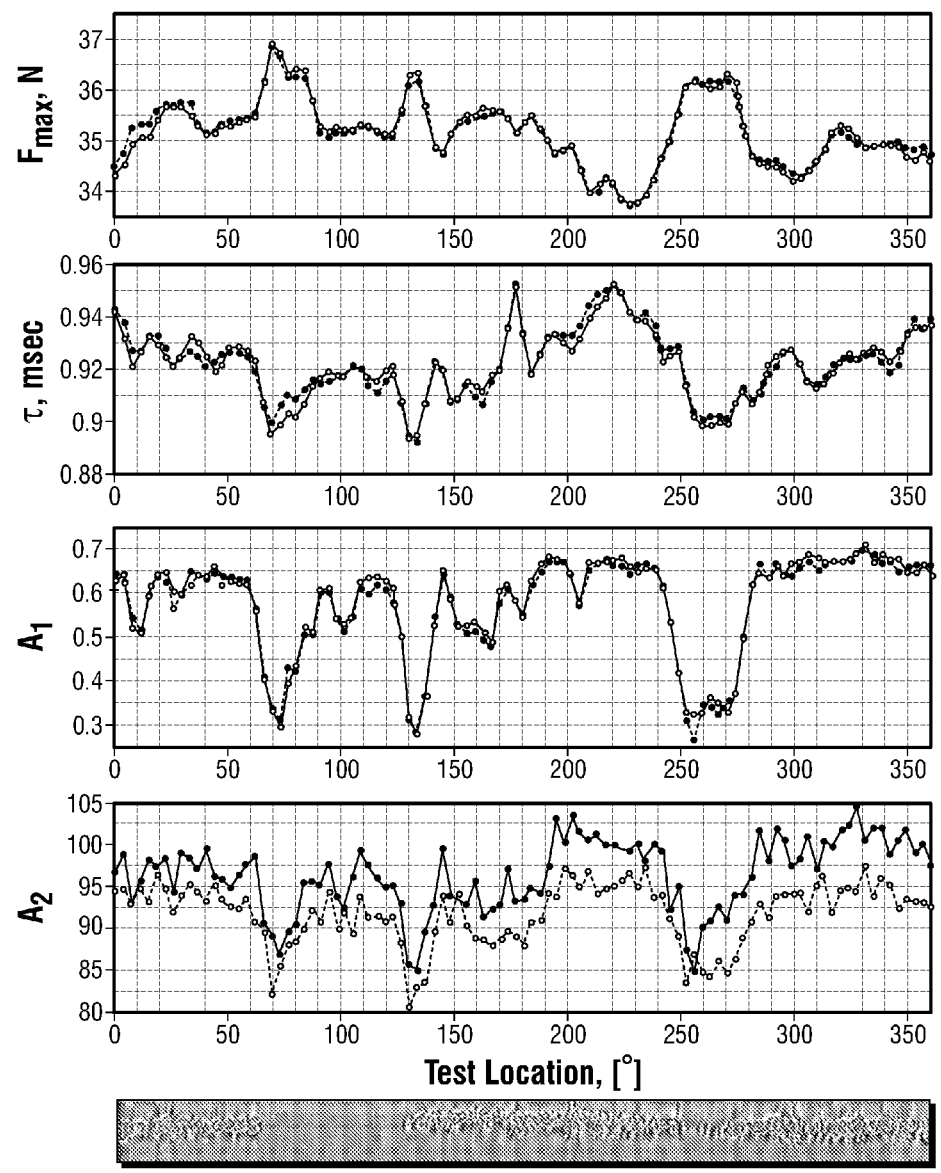
FIGS. 37 and 38 show anomaly discriminators measured on a representative tire shoulder.
Figure 38:
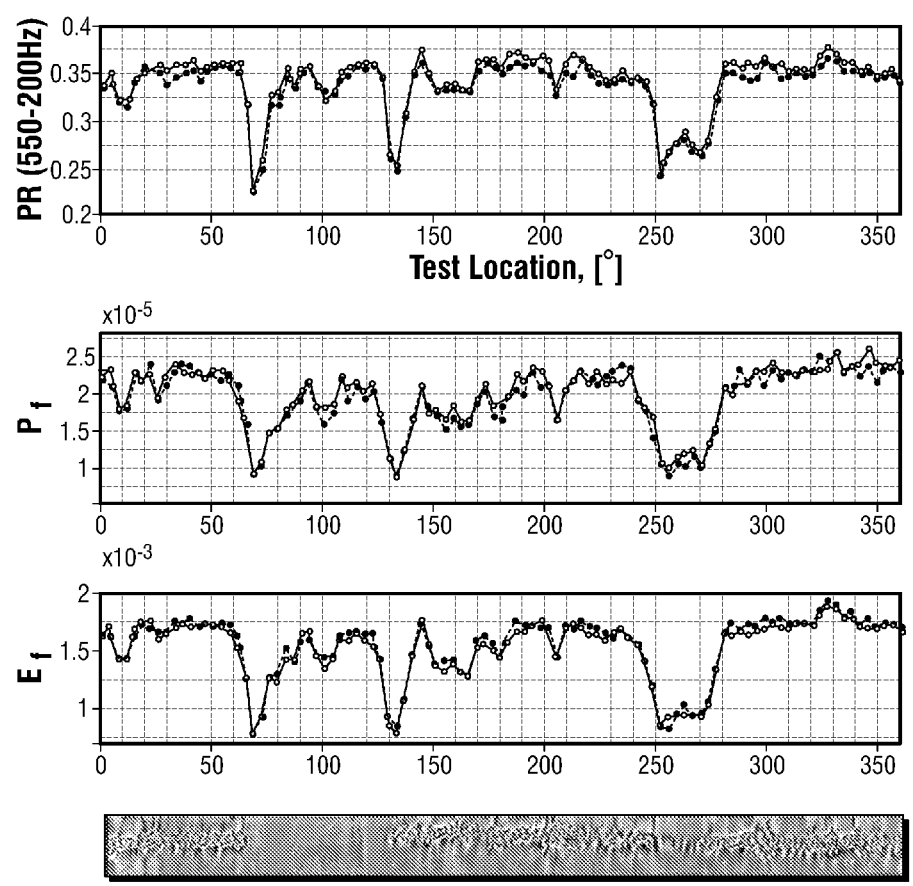

FIG. 36 shows the influence of the impact location on the peak sound amplitude measured from a shoulder of an extensively irregular tire. Each curve represents 101 measurements at the corresponding impact location for the entire circumference, with two repetitions at the initial test location. For the cracked areas, the peak sound amplitudes measured at x=0 mm show much larger discrepancy between the irregular areas and the integral areas. For example, the amplitudes measured around 250° are as low as about 0.4V but as high as 1.4V near 200°. The only mismatches between the amplitudes and the shearography are the regions between about 75° and 120° degree, where the shearography testing fails due to the surface anomaly. This suggests the advantage of the impact acoustic method over the shearography imaging method, since surface anomalies can affect shearography testing results. The presently disclosed impact acoustic method is normally only affected by local surface anomalies. The testing results over this specific region indicate that there are embedded anomalies that are not discovered by shearography. All of the impact acoustic discriminators were extracted for each measurement from the representative tire sample as plotted in FIGS. 37 and 38. Each plot is presented with results from two independent repetitions, where there are 101 measurements around the entire circumference for each repetition.

To combine seven discriminators into a single robust anomaly index (DI), the most intuitive method is to calculate the weighted mean (e.g., calculate and average the normalized discriminators). The DI can be calculated to perform a scaling to put the original discriminators into the [0, 1] range denoted as normalized discriminators (where 0 stands for regular and 1 for most severely irregular).

Figure 39:
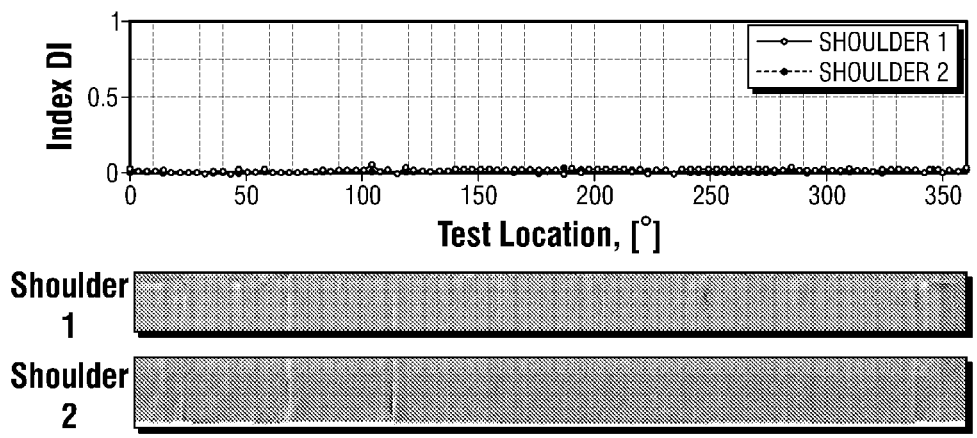
FIGS. 39 and 40 show anomaly indices for a brand new tire and for a tire with small discontinuous cracks in one shoulder, respectively.
Figure 40:
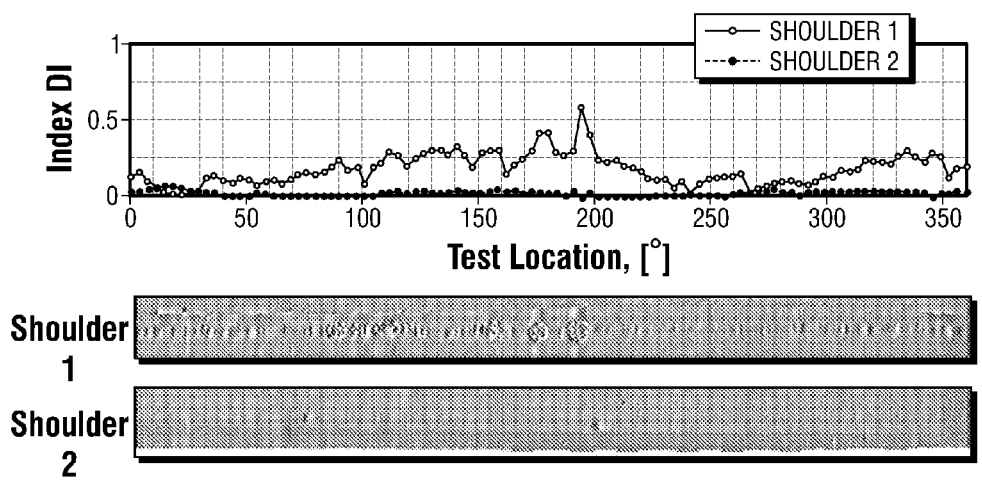

For a brand new tire in FIG. 39, the DIs are almost zero for both shoulders. In FIG. 40, discontinuous speckles are shown in a shearography image of the first shoulder, indicating initiation of belt edge separations in the shoulder area. The impact acoustic indices pointed out the two butterfly shaped speckles around 180° in the first shoulder. The DI values are generally around 0.25 for this shoulder and almost zero for the second shoulder, showing good contrasts between irregular and regular conditions. A significant point of the integration method is that tires of different constructions, and with the same inner diameter having a buffed tread, share a single set of parameters for normalization, which is of practical worth to propagate the method to larger populations of tires for anomaly inspection.

At least one of the acoustic transducer (e.g., one or microphones such as microphone 106 shown in FIG. 31) and the force transducer (e.g., a load cell incorporated with the impactor such as impactor 104 shown in FIG. 31) may be in communication with one or more computing devices for generating the anomaly index. At least one of the acoustic transducer and the force transducer may be a network-connected device in communication with the computing devices. A platform may be provided that includes at least one of a server in communication with the network-connected devices and an engine. The engine may be employed to access the ANN for training and prediction of anomaly indicators and/or to record test data as each tire is tested. The engine may also be configured to compute discriminator quantities based upon the detected sound waves and the force signal. At least one stored discriminator quantity may be compared with at least one calculated discriminator quantity and, based upon the comparing, an integrity of the tire determined.

The server may be further configured to facilitate communication between at least one of the transducers and one or more of the computing devices. A database may be built and accessed that includes stored discriminator quantities and calculated discriminator quantities of transducer outputs that can be generated for intended tire integrity. For example, in some embodiments, the stored discriminator quantities may be representative of a tire having no anomalies or irregularities. In some embodiments, the stored discriminator quantities may also include previously calculated discriminator quantities representative of varying degrees of irregularity. Test data from a tire being tested may be uploaded through the server and stored on the database for calculating the calculated discriminator quantities and comparing these with the stored discriminator quantities. One or more representations may be generated of the calculated discriminator quantities.

The engine may be further configured to generate a notification regarding the integrity of a tire being tested. The notification may notify a user with updated tire test data and updated anomaly indices corresponding to tire integrity.

The presently disclosed invention effectively detects anomalies using impact signals. The methodology for anomaly detection is based upon comparison of a current sensor response with a previously developed baseline sensor response from a regular structure (i.e., one lacking anomalies). The analysis of the experimental data is carried out in both microphone and load cell signals, and the approaches involved are time-domain and frequency-domain analysis.

At least some of the various techniques described herein may be implemented in connection with hardware or software or, where appropriate, with a combination of both. For example, electrical data processing functionality may be used to implement any aspect of discriminator derivation and index computation, including implementation in connection with a computing device (including a mobile networking apparatus) that includes hardware, software, or, where appropriate, a combination of both. The processing functionality may correspond to any type of computing device that includes one or more processing devices. The computing device can include any type of computer, computer system or other programmable electronic device, including a client computer, a server computer, a portable computer (including a laptop and a tablet), a handheld computer, a mobile phone (including a smart phone), a gaming device, an embedded controller, a near-field communication device, a device with applications implemented at least partly using a cloud service, and any combination and/or equivalent thereof (including touchless devices). Moreover, the computing device may be implemented using one or more networked computers, e.g., in a cluster or other distributed computing system. The network may be a LAN, a WAN, a SAN, a wireless network, a cellular network, radio links, optical links and/or the Internet, although the network is not limited to these network selections.

By training an ANN to obtain baseline data, a healthy tire will correlate well when compared to another healthy tire, yet not in the presence of an internal change or anomaly. Both time and frequency domain input data that were previously used as individual data for analysis may be integrated as inputs of the ANN. When the ANN is used to process both data sets in an integrated manner, increased values of the processed test signal correlate well with tire segments possessing anomalies and irregularities. This analysis provides a unified model for a variety of tire types. An apparatus and method is thereby provided for identifying internal anomalies in used tire casings at a lower cost and higher accuracy than existing methods.

It is further understood that the presently disclosed methods are contemplated for use on tires that have previously been subject to one or more retread processes, either as disclosed herein or according to one or more other amenable retreading methods. It is understood, however, that the presently disclosed methods may be employed on tires that have never been retread. The presently disclosed invention may be utilized in association with retreaded heavy duty truck or trailer tires and any other tire type, including but not limited to light truck, off-road, ATV, bus, aircraft, agricultural, mining, bicycle, motorcycle and passenger vehicle tires.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Also, the dimensions and values disclosed herein are not limited to a specified unit of measurement. For example, dimensions expressed in English units are understood to include equivalent dimensions in metric and other units (e.g., a dimension disclosed as "1 inch" is intended to mean an equivalent dimension of "2.5 cm").

As used herein, the term "method" or "process" refers to one or more steps that may be performed in other ordering than shown without departing from the scope of the presently disclosed invention. As used herein, the term "method" or "process" may include one or more steps performed at least by one electronic or computer-based apparatus. Any sequence of steps is exemplary and is not intended to limit methods described herein to any particular sequence, nor is it intended to preclude adding steps, omitting steps, repeating steps, or performing steps simultaneously.

The terms "a," "an," and the singular forms of words shall be taken to include the plural form of the same words, such that the terms mean that one or more of something is provided. The terms "at least one" and "one or more" are used interchangeably. Ranges that are described as being "between a and b" are inclusive of the values for "a" and "b."

As used herein, the term "process" or "method" refers to one or more steps that may be performed in other ordering than shown without departing from the scope of the invention. Also, some steps may be optional and may be omitted. Some or all steps may be performed by at least one computer having a processor for executing instructions that carry out the steps.

Every document cited herein, including any cross-referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosed apparatus have been illustrated and described, it will be understood that various changes, additions and modifications can be made without departing from the spirit and scope of the present disclosure. Accordingly, no limitation should be imposed on the scope of the presently disclosed invention, except as set forth in the accompanying claims.

What is claimed is:

1. An impact-acoustic method for testing a tire, comprising:
    providing an actuatable impactor disposed proximate an impact area whereupon the impactor strikes the tire;
    providing an acoustic transducer disposed proximate the impact area on a common side of the tire with the impactor, with the acoustic transducer receiving one or more sound waves generated when the impactor strikes the impact area and generating corresponding acoustic signals;
    providing a force transducer disposed proximate the impact area for measuring one or more dynamic forces and generating corresponding force signals indicative of impact force, wherein the force transducer is incorporated into the impactor such that the force transducer moves towards the impact area when the impactor strikes the impact area;
    providing a tire on a test platform such that the impactor strikes the impact area during actuation thereof;

calculating a plurality of discriminator quantities from the acoustic signals and the force signals; and comparing calculated discriminator quantities with stored discriminator quantities to determine whether an anomaly is present in the tire.

2. The impact-acoustic method of claim 1, further comprising providing one or more computing devices in communication with at least one of the acoustic transducer and the force transducer, wherein the one or more computing devices includes instructions for performing at least one of transferring data from at least one of the acoustic transducer and the force transducer and controlling one or both of the acoustic transducer and the force transducer either directly or indirectly.

3. The impact-acoustic method of claim 2, wherein each of the calculated discriminator quantities and the stored discriminator quantities includes one or more quantities of peak impact force, impact duration, area under initial contact sound, free vibration energy, accumulative power ratio, power spectrum local peak magnitude and accumulated spectral energy.

4. The impact-acoustic method of claim 2, wherein the stored discriminator quantities are representative of tire integrity of previously tested tires.

5. An impact-acoustic method for testing a tire, comprising:

providing an actuatable impactor disposed proximate an impact area whereupon the impactor strikes the tire;

providing an acoustic transducer disposed proximate the impact area on a common side of the tire with the impactor, with the acoustic transducer receiving one or more sound waves generated when the impactor strikes the impact area and generating corresponding acoustic signals;

providing a force transducer disposed proximate the impact area for measuring one or more dynamic forces and generating corresponding force signals indicative of impact force;

providing a tire on a test platform such that the impactor strikes the impact area during actuation thereof;

calculating a plurality of discriminator quantities from the acoustic signals and the force signals;

comparing calculated discriminator quantities with stored discriminator quantities to determine whether an anomaly is present in the tire;

providing one or more computing devices in communication with at least one of the acoustic transducer and the force transducer, wherein the one or more computing devices includes instructions for performing at least one of transferring data from at least one of the acoustic transducer and the force transducer and controlling one or both of the acoustic transducer and the force transducer either directly or indirectly;

wherein the stored discriminator quantities are representative of tire integrity of previously tested tires; and generating an anomaly index from weighted averaging of the calculated discriminator quantities as an indicator of tire integrity.

6. The impact-acoustic method of claim 5, wherein the impact area comprises a targeted area of a tire casing and the acoustic transducer is either disposed at a known distance from the targeted area or moved along with the impactor as the impactor strikes the impact area.

7. The impact-acoustic method of claim 6, wherein:
the impactor comprises an impactor generating an input pressure wave;

the acoustic transducer comprises one or more microphones; and the force transducer comprises a low mass load cell incorporated with the impactor.

8. The impact-acoustic method of claim 6, wherein at least one of the acoustic transducer and the force transducer is a network-connected device, and the method further includes providing a platform including at least one of:

a server in communication with at least one network-connected device; and an engine configured to perform at least one of:
accessing at least one artificial neural network (ANN) for training and predicting anomaly indicators;
recording test data as each tire is tested;
computing discriminator quantities based upon the detected sound waves and the force signals;
comparing at least one stored discriminator quantity with at least one calculated discriminator quantity; and
based upon the comparing, determining tire integrity.

9. The impact-acoustic method of claim 8, wherein the server is configured to perform actions comprising at least one of:

communicating over a network;
facilitating communication between the at least one network-connected device and the one or more computing devices;
building and accessing a database of stored discriminator quantities and calculated discriminator quantities of transducer outputs that can be generated for intended tire integrity;
uploading test data for storage on the database; and
generating one or more representations of one or more of the calculated discriminator quantities.

10. The impact-acoustic method of claim 9, wherein the engine is further configured to generate a notification that notifies a user with updated tire test data and updated anomaly indices corresponding to tire integrity.

11. A tire anomaly detection system, comprising a tire support system comprising a test platform; and an impact system, comprising:
an actuatable impactor disposed proximate an impact area whereupon the impactor strikes a tire placed on the test platform;
an acoustic transducer disposed proximate the impact area on a common side of the tire with the impactor, with the acoustic transducer receiving one or more sound waves generated when the impactor strikes the impact area and generating corresponding acoustic signals indicative of the received sound waves; and
a force transducer disposed proximate the impact area for measuring one or more dynamic forces and generating corresponding force signals indicative of impact force, wherein the force transducer is incorporated into the impactor such that the force transducer moves towards the impact area when the impactor strikes the impact area;
wherein a plurality of discriminator quantities are calculated from the acoustic signals and the force signals, and the calculated discriminator quantities are compared with stored discriminator quantities to determine whether an anomaly is present in the tire.

12. The tire anomaly detection system of claim 11, further comprising one or more computing devices in communication with at least one of the acoustic transducer and the force transducer.

13. The tire anomaly detection system of claim 12, wherein each of the calculated discriminator quantities and the stored discriminator quantities includes one or more quantities of peak impact force, impact duration, area under initial contact sound, free vibration energy, accumulative power ratio, power spectrum local peak magnitude and accumulated spectral energy.

14. The tire anomaly detection system of claim 13, wherein the stored discriminator quantities are representative of tire integrity of previously tested tires.

15. A tire anomaly detection system, comprising a tire support system comprising a test platform; and
    an impact system, comprising:
    an actuatable impactor disposed proximate an impact area whereupon the impactor strikes a tire placed on the test platform;
    an acoustic transducer disposed proximate the impact area on a common
    side of the tire with the impactor, with the acoustic transducer receiving one or more sound waves generated when the impactor strikes the impact area and generating corresponding acoustic signals indicative of the received sound waves;
    a force transducer disposed proximate the impact area for measuring one or more dynamic forces and generating corresponding force signals indicative of impact force;
    wherein a plurality of discriminator quantities are calculated from the acoustic signals and the force signals, and the calculated discriminator quantities are compared with stored discriminator quantities to determine whether an anomaly is present in the tire; and
    one or more computing devices in communication with at least one of the acoustic transducer and the force transducer;
    wherein each of the calculated discriminator quantities and the stored discriminator quantities includes one or more quantities of peak impact force, impact duration, area under initial contact sound, free vibration energy, accumulative power ratio, power spectrum local peak magnitude and accumulated spectral energy;
    wherein an anomaly index is calculated from a weighted averaging of the calculated discriminator quantities as an indicator of tire integrity.

16. The tire anomaly detection system of claim 15, wherein the impact area comprises a targeted area of a tire casing and the acoustic transducer is either disposed at a fixed distance from the targeted area or moved along with the impactor as the impactor strikes the impact area.

17. The tire anomaly detection system of claim 16, wherein:
    the impactor comprises an impactor generating an input pressure wave:
    the acoustic transducer comprises one or more microphones; and
    the force transducer comprises a low mass load cell incorporated with the impactor.

18. The tire anomaly detection system of claim 17, comprising one or more test platforms, wherein at least one test platform includes a tire rotation system.

19. The tire anomaly detection system of claim 16, wherein at least one of the acoustic transducer and the force transducer is a network-connected device, and the system further comprises a platform including at least one of:
    a server in communication with at least one network-connected device; and
    an engine configured to perform at least one of:
    accessing at least one artificial neural network (ANN) for training and predicting anomaly indicators;
    recording test data as each tire is tested;
    computing discriminator quantities based upon the detected sound waves and the force signals;
    comparing at least one stored discriminator quantity with at least one calculated discriminator quantity; and
    based upon the comparing, determining tire integrity.

20. The tire anomaly detection system of claim 19, wherein the server is configured to perform actions comprising at least one of:
    communicating over a network;
    facilitating communication between the at least one network-connected device and the one or more computing devices;
    building and accessing a database of stored discriminator quantities and calculated discriminator quantities of transducer outputs that can be generated for intended tire integrity;
    uploading test data for storage on the database; and
    generating one or more representations of one or more of the calculated discriminator quantities.

21. The tire anomaly detection system of claim 20, wherein the engine is further configured to generate a notification that notifies a user with updated tire test data and updated anomaly indices corresponding to tire integrity.

22. A tire anomaly detection system, comprising:
    a tire support structure for supporting a tire during testing;
    an impactor disposed proximate the tire for impacting the tire at one or more locations;
    an acoustic transducer disposed proximate the impactor for receiving a sound wave when the impactor contacts the tire;
    a force transducer for measuring one or more dynamic forces at locations of impactor contact and generating corresponding force signals indicative of impact force, wherein the force transducer is incorporated into the impactor such that the force transducer moves towards the locations of impactor contact when the impactor impacts the tire at one or more locations; and
    one or more computing devices each having a processor with instructions for calculating a plurality of discriminator quantities from the sound wave and the force signals and instructions for comparing the calculated discriminator values with stored discriminator values indicative of an anomaly in the tire.

23. The tire anomaly detection system of claim 22, wherein each of the calculated discriminator quantities and the stored discriminator quantities includes one or more quantities of peak impact force, impact duration, area under initial contact sound, free vibration energy, accumulative power ratio, power spectrum local peak magnitude and accumulated spectral energy.

24. The tire anomaly detection system of claim 23, wherein the stored discriminator quantities are representative of tire integrity of previously tested tires.

25. A tire anomaly detection system, comprising:
    a tire support structure for supporting a tire during testing;
    an impactor disposed proximate the tire for impacting the tire at one or more locations;
    an acoustic transducer disposed proximate the impactor for receiving a sound wave when the impactor contacts the tire;
    a force transducer for measuring one or more dynamic forces at locations of impactor contact and generating corresponding force signals indicative of impact force; and
    one or more computing devices each having a processor with instructions for calculating a plurality of discriminator quantities from the sound wave and the force signals and instructions for comparing the calculated discriminator values with stored discriminator values indicative of an anomaly in the tire;

wherein the instructions calculate an anomaly index from a weighted averaging of the calculated discriminator quantities as an indicator of tire integrity.

26. The system of claim 25, wherein the system further comprises a server in communication with at least one network-connected transducer, the server configured to perform actions comprising:

accessing the system over a network via a network interface; and obtaining information from at least one transducer when the impactor contacts the tire.

* * * * *